(12) United States Patent
Martin et al.

(10) Patent No.: US 8,328,861 B2
(45) Date of Patent: Dec. 11, 2012

(54) DELIVERY SYSTEM AND METHOD FOR BIFURCATED GRAFT

(75) Inventors: Gerald Ray Martin, Redwood City, CA (US); James R. Watson, Santa Rosa, CA (US); Isaac J. Zacharias, Pleasanton, CA (US)

(73) Assignee: Trivascular, Inc., Santa Rosa, CA (US)

( * ) Notice: Subject to any disclaimer, the term of this patent is extended or adjusted under 35 U.S.C. 154(b) by 818 days.

(21) Appl. No.: 11/941,434

(22) Filed: Nov. 16, 2007

(65) Prior Publication Data

US 2009/0132026 A1    May 21, 2009

(51) Int. Cl.
*A61F 2/06* (2006.01)
(52) U.S. Cl. ..................................... 623/1.12; 623/1.11
(58) Field of Classification Search ................ 623/1, 11, 623/1.12, 1.11; 606/108
See application file for complete search history.

(56) References Cited

U.S. PATENT DOCUMENTS

| | | |
|---|---|---|
| 3,076,737 A | 2/1963 | Roberts |
| 3,540,431 A | 11/1970 | Uddin |
| 3,631,854 A | 1/1972 | Fryer et al. |
| 3,657,744 A | 4/1972 | Ersek |
| 3,669,586 A | 6/1972 | Kramer |
| 3,814,137 A | 6/1974 | Martinez |
| 3,818,511 A | 6/1974 | Goldberg et al. |
| 3,902,198 A | 9/1975 | Cooper |
| 3,991,767 A | 11/1976 | Miller et al. |
| 4,096,227 A | 6/1978 | Gore |
| 4,110,392 A | 8/1978 | Yamazaki |
| 4,140,126 A | 2/1979 | Choudhury |
| 4,183,102 A | 1/1980 | Guiset |
| 4,187,390 A | 2/1980 | Gore |
| 4,208,745 A | 6/1980 | Okita |
| 4,214,587 A | 7/1980 | Sakura, Jr. |
| 4,229,838 A | 10/1980 | Mano |
| 4,248,924 A | 2/1981 | Okita |
| 4,385,093 A | 5/1983 | Hubis |
| 4,416,028 A | 11/1983 | Eriksson et al. |

(Continued)

FOREIGN PATENT DOCUMENTS

EP    0646365    4/1995

(Continued)

OTHER PUBLICATIONS

US 6,413,270, 7/2002, Thornton et al. (withdrawn).

(Continued)

*Primary Examiner* — Darwin Erezo
(74) *Attorney, Agent, or Firm* — Grant Anderson LLP

(57) ABSTRACT

A delivery system and method for delivering a bifurcated intracorporeal device. The delivery system comprises a shaft having a distal section supporting a primary support member positioned to be disposed within at least a primary portion of the bifurcated intracorporeal device and a secondary support member extending within a secondary portion of the bifurcated intracorporeal device. At least one belt is configured to be circumferentially disposed about a portion of the secondary support member so to at least partially constrain the secondary portion of the bifurcated intracorporeal device. A tube defining a lumen is secured relative to the secondary support member. A release member is configured to engage and releasably secure the belt in a constraining configuration. The release member extends through at least a portion of the tube lumen such that the release member is accessible adjacent a proximal end of the tube.

16 Claims, 20 Drawing Sheets

U.S. PATENT DOCUMENTS

| | | |
|---|---|---|
| 4,434,797 A | 3/1984 | Silander |
| 4,459,252 A | 7/1984 | MacGregor |
| 4,474,630 A | 10/1984 | Planck et al. |
| 4,478,665 A | 10/1984 | Hubis |
| 4,482,516 A | 11/1984 | Bowman et al. |
| 4,497,074 A | 2/1985 | Rey et al. |
| 4,503,569 A | 3/1985 | Dotter |
| 4,512,338 A | 4/1985 | Balko et al. |
| 4,550,447 A | 11/1985 | Seiler, Jr. et al. |
| 4,552,707 A | 11/1985 | How |
| 4,562,596 A | 1/1986 | Kornberg |
| 4,577,631 A | 3/1986 | Kreamer |
| 4,580,568 A | 4/1986 | Gianturco |
| 4,592,754 A | 6/1986 | Gupte et al. |
| 4,617,932 A | 10/1986 | Kornberg |
| 4,647,416 A | 3/1987 | Seiler, Jr. et al. |
| 4,655,769 A | 4/1987 | Zachariades |
| 4,655,771 A | 4/1987 | Wallsten |
| 4,665,906 A | 5/1987 | Jervis |
| 4,705,517 A | 11/1987 | DiPisa, Jr. |
| 4,731,073 A | 3/1988 | Robinson |
| 4,733,665 A | 3/1988 | Palmaz |
| 4,739,762 A | 4/1988 | Palmaz |
| 4,740,207 A | 4/1988 | Kreamer |
| 4,743,480 A | 5/1988 | Campbell et al. |
| 4,760,102 A | 7/1988 | Moriyama et al. |
| 4,776,337 A | 10/1988 | Palmaz |
| 4,787,899 A | 11/1988 | Lazarus |
| 4,816,028 A | 3/1989 | Kapadia et al. |
| 4,830,003 A | 5/1989 | Wolff et al. |
| 4,856,516 A | 8/1989 | Hillstead |
| 4,871,365 A | 10/1989 | Dumican |
| 4,877,661 A | 10/1989 | House et al. |
| 4,902,423 A | 2/1990 | Bacino |
| 4,932,938 A | 6/1990 | Goldberg et al. |
| 4,941,870 A | 7/1990 | Okada et al. |
| 4,955,899 A | 9/1990 | Della et al. |
| 4,957,669 A | 9/1990 | Primm |
| 4,985,296 A | 1/1991 | Mortimer, Jr. |
| 4,994,071 A | 2/1991 | MacGregor |
| 4,994,077 A | 2/1991 | Dobben |
| 5,019,090 A | 5/1991 | Pinchuk |
| 5,041,126 A | 8/1991 | Gianturco |
| 5,052,998 A | 10/1991 | Zimmon |
| 5,059,211 A | 10/1991 | Stack et al. |
| 5,064,435 A | 11/1991 | Porter |
| 5,098,625 A | 3/1992 | Huang et al. |
| 5,100,422 A | 3/1992 | Berguer et al. |
| 5,104,399 A | 4/1992 | Lazarus |
| 5,104,400 A | 4/1992 | Berguer et al. |
| 5,104,404 A | 4/1992 | Wolff |
| 5,108,424 A | 4/1992 | Hoffman, Jr. et al. |
| 5,110,527 A | 5/1992 | Harada et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,139,480 A | 8/1992 | Hickle et al. |
| 5,150,304 A | 9/1992 | Berchem et al. |
| 5,151,105 A | 9/1992 | Kwan-Gett |
| 5,152,782 A | 10/1992 | Kowligi et al. |
| 5,156,620 A | 10/1992 | Pigott |
| 5,163,955 A | 11/1992 | Love |
| 5,167,614 A | 12/1992 | Tessmann |
| 5,171,262 A | 12/1992 | MacGregor |
| 5,192,310 A | 3/1993 | Herweck et al. |
| 5,195,984 A | 3/1993 | Schatz |
| 5,197,976 A | 3/1993 | Herweck et al. |
| 5,197,978 A | 3/1993 | Hess |
| 5,201,757 A | 4/1993 | Heyn et al. |
| 5,202,352 A | 4/1993 | Okada et al. |
| 5,207,695 A | 5/1993 | Trout, III |
| 5,217,483 A | 6/1993 | Tower |
| 5,219,355 A | 6/1993 | Parodi et al. |
| 5,226,913 A | 7/1993 | Pinchuk |
| 5,234,456 A | 8/1993 | Silvestrini |
| 5,250,059 A | 10/1993 | Andreas et al. |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,290,305 A | 3/1994 | Inoue |
| 5,292,331 A | 3/1994 | Boneau |
| 5,304,200 A | 4/1994 | Spaulding |
| 5,314,472 A | 5/1994 | Fontaine |
| 5,316,023 A | 5/1994 | Palmaz et al. |
| 5,320,100 A | 6/1994 | Herweck et al. |
| 5,321,109 A | 6/1994 | Bosse et al. |
| 5,330,528 A | 7/1994 | Lazim |
| 5,334,164 A | 8/1994 | Guy et al. |
| 5,334,201 A | 8/1994 | Cowan |
| 5,344,426 A | 9/1994 | Lau et al. |
| 5,344,444 A | 9/1994 | Glastra |
| 5,344,451 A | 9/1994 | Dayton |
| 5,350,398 A | 9/1994 | Pavcnik |
| 5,354,310 A | 10/1994 | Garnic et al. |
| 5,354,329 A | 10/1994 | Whalen |
| 5,360,443 A | 11/1994 | Barone et al. |
| 5,365,996 A | 11/1994 | Crook |
| 5,366,504 A | 11/1994 | Andersen et al. |
| 5,370,682 A | 12/1994 | Schmitt |
| 5,370,691 A | 12/1994 | Samson |
| 5,374,473 A | 12/1994 | Knox et al. |
| 5,382,261 A | 1/1995 | Palmaz |
| 5,383,892 A | 1/1995 | Cardon et al. |
| 5,383,928 A | 1/1995 | Scott et al. |
| 5,387,235 A | 2/1995 | Chuter et al. |
| 5,389,106 A | 2/1995 | Tower et al. |
| 5,391,147 A | 2/1995 | Imran et al. |
| 5,397,345 A | 3/1995 | Lazarus |
| 5,405,377 A | 4/1995 | Cragg |
| 5,405,378 A | 4/1995 | Strecker |
| 5,405,379 A | 4/1995 | Lane |
| 5,411,550 A | 5/1995 | Herweck et al. |
| 5,415,634 A | 5/1995 | Glynn et al. |
| 5,423,851 A | 6/1995 | Samuels |
| 5,433,909 A | 7/1995 | Martakos et al. |
| 5,437,900 A | 8/1995 | Kuzowski |
| 5,441,515 A | 8/1995 | Khosravi et al. |
| 5,443,458 A | 8/1995 | Eury |
| 5,443,498 A | 8/1995 | Fontaine |
| 5,445,646 A | 8/1995 | Euteneuer et al. |
| 5,447,152 A | 9/1995 | Kohsai et al. |
| 5,449,373 A | 9/1995 | Pinchasik et al. |
| 5,456,713 A | 10/1995 | Chuter |
| 5,464,419 A | 11/1995 | Glastra |
| 5,464,449 A | 11/1995 | Ryan et al. |
| 5,466,509 A | 11/1995 | Kowllgl et al. |
| 5,474,824 A | 12/1995 | Martakos et al. |
| 5,476,506 A | 12/1995 | Lunn |
| 5,476,589 A | 12/1995 | Bacino |
| 5,478,330 A | 12/1995 | Imran et al. |
| 5,480,423 A | 1/1996 | Ravenscroft et al. |
| 5,489,295 A | 2/1996 | Piplani et al. |
| 5,505,887 A | 4/1996 | Zdrahala et al. |
| 5,507,769 A | 4/1996 | Marin et al. |
| 5,507,770 A | 4/1996 | Turk |
| 5,512,360 A | 4/1996 | King |
| 5,514,154 A | 5/1996 | Lau et al. |
| 5,522,880 A | 6/1996 | Barone et al. |
| 5,522,881 A | 6/1996 | Lentz |
| 5,522,883 A | 6/1996 | Slater et al. |
| 5,524,633 A | 6/1996 | Heaven et al. |
| 5,527,353 A | 6/1996 | Schmitt |
| 5,527,355 A | 6/1996 | Ahn |
| 5,529,653 A | 6/1996 | Glastra |
| 5,529,820 A | 6/1996 | Nomi et al. |
| 5,534,024 A | 7/1996 | Rogers et al. |
| 5,536,274 A | 7/1996 | Neuss |
| 5,545,135 A | 8/1996 | Iacob et al. |
| 5,549,662 A | 8/1996 | Fordenbacher |
| 5,549,663 A | 8/1996 | Cottone, Jr. |
| 5,552,100 A | 9/1996 | Shannon et al. |
| 5,554,180 A | 9/1996 | Turk |
| 5,554,181 A | 9/1996 | Das |
| 5,554,183 A | 9/1996 | Nazari |

| | | |
|---|---|---|
| 5,554,185 A | 9/1996 | Block et al. |
| 5,556,414 A | 9/1996 | Turi |
| 5,556,426 A | 9/1996 | Popadiuk et al. |
| 5,560,986 A | 10/1996 | Mortimer, Jr. |
| 5,562,697 A | 10/1996 | Christiansen |
| 5,562,724 A | 10/1996 | Vorwerk et al. |
| 5,562,726 A | 10/1996 | Chuter |
| 5,562,727 A | 10/1996 | Turk et al. |
| 5,562,728 A | 10/1996 | Lazarus et al. |
| 5,569,295 A | 10/1996 | Lam |
| 5,571,171 A | 11/1996 | Barone et al. |
| 5,571,172 A | 11/1996 | Chin |
| 5,571,173 A | 11/1996 | Parodi |
| 5,575,817 A | 11/1996 | Martin |
| 5,575,818 A | 11/1996 | Pinchuk |
| 5,578,071 A | 11/1996 | Parodi |
| 5,578,072 A | 11/1996 | Barone et al. |
| 5,588,964 A | 12/1996 | Imran et al. |
| 5,591,195 A | 1/1997 | Taheri et al. |
| 5,591,197 A | 1/1997 | Orth et al. |
| 5,591,229 A | 1/1997 | Parodi |
| 5,597,378 A | 1/1997 | Jervis |
| 5,603,721 A | 2/1997 | Lau et al. |
| 5,607,478 A | 3/1997 | Lentz et al. |
| 5,609,624 A | 3/1997 | Kalis |
| 5,609,625 A | 3/1997 | Piplani et al. |
| 5,609,627 A | 3/1997 | Goicoechea et al. |
| 5,609,628 A | 3/1997 | Keranen |
| 5,609,629 A | 3/1997 | Fearnont |
| 5,612,885 A | 3/1997 | Love |
| 5,618,301 A | 4/1997 | Hauenstein et al. |
| 5,620,763 A | 4/1997 | House et al. |
| 5,626,599 A | 5/1997 | Bourne et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,632,772 A | 5/1997 | Alcime et al. |
| 5,632,840 A | 5/1997 | Campbell |
| 5,639,278 A | 6/1997 | Dereume et al. |
| 5,641,373 A | 6/1997 | Shannon et al. |
| 5,645,915 A | 7/1997 | Kranzler et al. |
| 5,649,978 A | 7/1997 | Samson |
| 5,653,745 A | 8/1997 | Trescony et al. |
| 5,653,746 A | 8/1997 | Schmitt |
| 5,656,029 A | 8/1997 | Imran et al. |
| 5,662,675 A | 9/1997 | Stockert et al. |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,451 A | 11/1997 | Lenker et al. |
| 5,683,453 A | 11/1997 | Palmaz |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,697,971 A | 12/1997 | Fischell et al. |
| 5,700,285 A | 12/1997 | Myers et al. |
| 5,707,378 A | 1/1998 | Ahn et al. |
| 5,707,388 A | 1/1998 | Lauterjung |
| 5,708,044 A | 1/1998 | Branca |
| 5,709,701 A | 1/1998 | Parodi |
| 5,709,703 A | 1/1998 | Lukie et al. |
| 5,712,315 A | 1/1998 | Dolan |
| 5,713,917 A | 2/1998 | Leonhardt et al. |
| 5,716,393 A | 2/1998 | Lindenberg et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,725,549 A | 3/1998 | Lam |
| 5,728,131 A | 3/1998 | Frantzen et al. |
| 5,733,303 A | 3/1998 | Israel et al. |
| 5,733,325 A | 3/1998 | Robinson et al. |
| 5,735,892 A | 4/1998 | Myers et al. |
| 5,735,893 A | 4/1998 | Lau et al. |
| 5,735,897 A | 4/1998 | Buirge |
| 5,741,324 A | 4/1998 | Glastra |
| 5,741,325 A | 4/1998 | Chaikof et al. |
| 5,747,128 A | 5/1998 | Campbell et al. |
| 5,749,880 A | 5/1998 | Banas et al. |
| 5,749,894 A | 5/1998 | Engelson |
| 5,749,920 A | 5/1998 | Quiachon et al. |
| 5,749,921 A | 5/1998 | Lenker et al. |
| 5,755,772 A | 5/1998 | Evans et al. |
| 5,755,776 A | 5/1998 | Al-Saadon |
| 5,766,203 A | 6/1998 | Imran et al. |
| 5,769,882 A | 6/1998 | Fogarty et al. |
| 5,769,885 A | 6/1998 | Quiachon et al. |
| 5,769,887 A | 6/1998 | Brown et al. |
| 5,772,884 A | 6/1998 | Tanaka et al. |
| 5,776,142 A | 7/1998 | Gunderson |
| 5,776,161 A | 7/1998 | Globerman |
| 5,776,183 A | 7/1998 | Kanesaka et al. |
| 5,780,807 A | 7/1998 | Saunders |
| 5,782,789 A | 7/1998 | Herweck et al. |
| 5,782,838 A | 7/1998 | Beyar et al. |
| 5,782,904 A | 7/1998 | White et al. |
| 5,782,909 A | 7/1998 | Quiachon et al. |
| 5,785,679 A | 7/1998 | Abolfathi et al. |
| 5,788,626 A | 8/1998 | Thompson |
| 5,789,047 A | 8/1998 | Sasaki et al. |
| 5,797,951 A | 8/1998 | Mueller |
| 5,798,924 A | 8/1998 | Eufinger et al. |
| 5,799,384 A | 9/1998 | Schwartz et al. |
| 5,800,508 A | 9/1998 | Goicoechea et al. |
| 5,800,512 A | 9/1998 | Lentz et al. |
| 5,800,515 A | 9/1998 | Nadal et al. |
| 5,800,518 A | 9/1998 | Piplani et al. |
| 5,800,522 A | 9/1998 | Campbell et al. |
| 5,800,524 A | 9/1998 | Borghi |
| 5,800,526 A | 9/1998 | Anderson et al. |
| 5,810,870 A | 9/1998 | Myers et al. |
| 5,810,872 A | 9/1998 | Kanesaka et al. |
| 5,814,405 A | 9/1998 | Branca et al. |
| 5,817,102 A | 10/1998 | Johnson et al. |
| 5,824,037 A | 10/1998 | Fogarty et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,046 A | 10/1998 | Smith et al. |
| 5,824,058 A | 10/1998 | Ravenscroft et al. |
| 5,827,289 A | 10/1998 | Reiley et al. |
| 5,827,310 A | 10/1998 | Marin et al. |
| 5,827,320 A | 10/1998 | Richter et al. |
| 5,827,321 A | 10/1998 | Roubin et al. |
| 5,833,651 A | 11/1998 | Donovan et al. |
| 5,833,707 A | 11/1998 | Mcintyre et al. |
| 5,836,964 A | 11/1998 | Richter et al. |
| 5,836,966 A | 11/1998 | St. Germain |
| 5,840,775 A | 11/1998 | Howard, Jr. et al. |
| 5,843,158 A | 12/1998 | Lenker et al. |
| 5,843,160 A | 12/1998 | Rhodes |
| 5,843,162 A | 12/1998 | Inoue |
| 5,843,164 A | 12/1998 | Frantzen et al. |
| 5,843,166 A | 12/1998 | Lentz et al. |
| 5,843,167 A | 12/1998 | Dwyer et al. |
| 5,843,170 A | 12/1998 | Ahn |
| 5,843,173 A | 12/1998 | Shannon et al. |
| 5,843,175 A | 12/1998 | Frantzen |
| 5,853,419 A | 12/1998 | Imran |
| 5,855,598 A | 1/1999 | Pinchuk |
| 5,858,556 A | 1/1999 | Eckert et al. |
| 5,861,027 A | 1/1999 | Trapp |
| 5,871,536 A | 2/1999 | Lazarus |
| 5,871,537 A | 2/1999 | Holman et al. |

| Patent No. | Date | Inventor |
|---|---|---|
| 5,871,538 A | 2/1999 | Dereume |
| 5,873,906 A | 2/1999 | Lau et al. |
| 5,876,432 A | 3/1999 | Lau et al. |
| 5,891,193 A | 4/1999 | Robinson et al. |
| 5,904,713 A | 5/1999 | Leschinsky |
| 5,906,619 A | 5/1999 | Olson et al. |
| 5,906,641 A | 5/1999 | Thompson et al. |
| 5,910,168 A | 6/1999 | Meyers et al. |
| 5,910,277 A | 6/1999 | Ishino et al. |
| 5,911,754 A | 6/1999 | Kanesaka et al. |
| 5,916,264 A | 6/1999 | Von Oepen et al. |
| 5,919,204 A | 7/1999 | Lukic et al. |
| 5,922,020 A | 7/1999 | Klein et al. |
| 5,925,061 A | 7/1999 | Ogi et al. |
| 5,925,075 A | 7/1999 | Myers et al. |
| 5,931,865 A | 8/1999 | Silverman et al. |
| 5,935,667 A | 8/1999 | Calcote et al. |
| 5,939,198 A | 8/1999 | Howard, Jr. et al. |
| 5,944,750 A | 8/1999 | Tanner et al. |
| 5,948,016 A | 9/1999 | Jang |
| 5,954,729 A | 9/1999 | Bachmann et al. |
| 5,955,016 A | 9/1999 | Goldfarb |
| 5,957,973 A | 9/1999 | Quiachon et al. |
| 5,961,545 A | 10/1999 | Lentz et al. |
| 5,961,546 A | 10/1999 | Robinson et al. |
| 5,968,068 A | 10/1999 | Dehdashtian et al. |
| 5,968,090 A | 10/1999 | Ratcliff et al. |
| 5,972,023 A | 10/1999 | Tanner et al. |
| 5,972,027 A | 10/1999 | Johnson |
| 5,972,441 A | 10/1999 | Campbell et al. |
| 5,976,155 A | 11/1999 | Foreman et al. |
| 5,976,179 A | 11/1999 | Inoue |
| 5,976,192 A | 11/1999 | McIntyre et al. |
| 5,976,650 A | 11/1999 | Campbell et al. |
| 5,980,530 A | 11/1999 | Willard et al. |
| 5,980,570 A | 11/1999 | Simpson |
| 5,984,955 A | 11/1999 | Wisselink |
| 5,984,956 A | 11/1999 | Tweden et al. |
| 5,984,964 A | 11/1999 | Roberts et al. |
| 5,989,287 A | 11/1999 | Yang et al. |
| 5,993,481 A | 11/1999 | Marcade et al. |
| 5,993,489 A | 11/1999 | Lewis et al. |
| 5,997,573 A | 12/1999 | Quijano et al. |
| 6,001,123 A | 12/1999 | Lau |
| 6,004,346 A | 12/1999 | Wolff et al. |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,015,432 A | 1/2000 | Rakos et al. |
| 6,017,362 A | 1/2000 | Lau |
| 6,017,364 A | 1/2000 | Lazarus |
| 6,019,778 A | 2/2000 | Wilson et al. |
| 6,019,779 A | 2/2000 | Thorud et al. |
| 6,019,787 A | 2/2000 | Richard et al. |
| 6,022,359 A | 2/2000 | Frantzen |
| 6,024,763 A | 2/2000 | Lenker et al. |
| 6,025,044 A | 2/2000 | Campbell et al. |
| 6,027,779 A | 2/2000 | Campbell et al. |
| 6,027,811 A | 2/2000 | Campbell et al. |
| 6,030,413 A | 2/2000 | Lazarus |
| 6,030,414 A | 2/2000 | Taheri |
| 6,030,415 A | 2/2000 | Chuter |
| 6,036,640 A | 3/2000 | Corace et al. |
| 6,036,702 A | 3/2000 | Bachinski et al. |
| 6,036,723 A | 3/2000 | Anidjar et al. |
| 6,036,724 A | 3/2000 | Lentz et al. |
| 6,036,725 A | 3/2000 | Avellanet |
| 6,039,754 A | 3/2000 | Caro |
| 6,039,758 A | 3/2000 | Quiachon et al. |
| 6,042,589 A | 3/2000 | Marianne |
| 6,042,605 A | 3/2000 | Martin et al. |
| 6,042,606 A | 3/2000 | Frantzen |
| 6,045,557 A | 4/2000 | White et al. |
| 6,048,484 A | 4/2000 | House et al. |
| 6,051,020 A | 4/2000 | Goicoechea et al. |
| 6,053,943 A | 4/2000 | Edwin et al. |
| 6,059,821 A | 5/2000 | Anidjar et al. |
| 6,059,823 A | 5/2000 | Holman et al. |
| 6,060,534 A | 5/2000 | Ronan et al. |
| 6,063,114 A | 5/2000 | Nash et al. |
| 6,068,626 A | 5/2000 | Harrington et al. |
| 6,070,589 A | 6/2000 | Keith et al. |
| 6,074,341 A | 6/2000 | Anderson et al. |
| 6,075,180 A | 6/2000 | Sharber et al. |
| 6,077,296 A | 6/2000 | Shokoohi et al. |
| 6,077,297 A | 6/2000 | Robinson et al. |
| 6,077,298 A | 6/2000 | Tu et al. |
| 6,090,128 A | 7/2000 | Douglas |
| 6,093,203 A | 7/2000 | Uflacker |
| 6,096,052 A | 8/2000 | Callister et al. |
| 6,096,070 A | 8/2000 | Ragheb et al. |
| 6,098,630 A | 8/2000 | Papazoglou |
| 6,102,918 A | 8/2000 | Kerr |
| 6,102,938 A | 8/2000 | Evans et al. |
| 6,102,940 A | 8/2000 | Robichon et al. |
| 6,103,172 A | 8/2000 | Newman et al. |
| 6,106,548 A | 8/2000 | Roubin et al. |
| 6,110,198 A | 8/2000 | Fogarty et al. |
| 6,113,628 A | 9/2000 | Borghi |
| 6,117,168 A | 9/2000 | Yang et al. |
| 6,123,722 A | 9/2000 | Fogarty et al. |
| 6,124,523 A | 9/2000 | Banas et al. |
| 6,126,685 A | 10/2000 | Lenker et al. |
| 6,129,756 A | 10/2000 | Kugler et al. |
| 6,132,457 A | 10/2000 | Chobotov |
| 6,132,459 A | 10/2000 | Piplani et al. |
| 6,139,572 A | 10/2000 | Campbell et al. |
| 6,142,973 A | 11/2000 | Carleton et al. |
| 6,143,014 A | 11/2000 | Dehdashtian et al. |
| 6,143,015 A | 11/2000 | Nobles |
| 6,143,016 A | 11/2000 | Bleam et al. |
| 6,143,021 A | 11/2000 | Staehle |
| 6,143,022 A | 11/2000 | Shull et al. |
| 6,146,389 A | 11/2000 | Geitz |
| 6,146,416 A | 11/2000 | Andersen et al. |
| 6,146,417 A | 11/2000 | Ischinger |
| 6,149,665 A | 11/2000 | Gabbay |
| 6,149,681 A | 11/2000 | Houser et al. |
| 6,149,682 A | 11/2000 | Frid |
| 6,152,944 A | 11/2000 | Holman et al. |
| 6,152,956 A | 11/2000 | Pierce |
| 6,156,063 A | 12/2000 | Douglas |
| 6,156,064 A | 12/2000 | Chouinard |
| 6,159,229 A | 12/2000 | Jendersee et al. |
| 6,159,237 A | 12/2000 | Alt et al. |
| 6,159,238 A | 12/2000 | Killion et al. |
| 6,159,239 A | 12/2000 | Greenhalgh |
| 6,159,565 A | 12/2000 | Campbell et al. |
| 6,162,243 A | 12/2000 | Gray et al. |
| 6,162,245 A | 12/2000 | Jayaraman |
| 6,162,246 A | 12/2000 | Barone |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,614 B1 | 1/2001 | Andersen et al. |
| 6,168,616 B1 | 1/2001 | Brown, III |
| 6,168,617 B1 | 1/2001 | Blaeser et al. |
| 6,168,618 B1 | 1/2001 | Frantzen |
| 6,168,619 B1 | 1/2001 | Dinh et al. |
| 6,168,620 B1 | 1/2001 | Kerr |
| 6,174,326 B1 | 1/2001 | Kitaoka et al. |
| 6,183,481 B1 | 2/2001 | Lee et al. |
| 6,183,504 B1 | 2/2001 | Inoue |
| 6,187,034 B1 | 2/2001 | Frantzen |
| 6,187,036 B1 | 2/2001 | Shaolian et al. |
| 6,187,054 B1 | 2/2001 | Colone et al. |
| 6,193,745 B1 | 2/2001 | Fogarty et al. |
| 6,196,230 B1 | 3/2001 | Hall et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,203,568 B1 | 3/2001 | Lombardi et al. |

| | | | | | | |
|---|---|---|---|---|---|---|
| 6,203,569 | B1 | 3/2001 | Wijay | 6,331,188 | B1 | 12/2001 | Lau et al. |
| 6,203,735 | B1 | 3/2001 | Edwin et al. | 6,331,190 | B1 | 12/2001 | Shokoohi et al. |
| 6,203,779 | B1 | 3/2001 | Ricci et al. | 6,331,191 | B1 | 12/2001 | Chobotov |
| 6,210,422 | B1 | 4/2001 | Douglas | 6,334,869 | B1 | 1/2002 | Leonhardt et al. |
| 6,210,434 | B1 | 4/2001 | Quiachon et al. | 6,336,937 | B1 | 1/2002 | Vonesh et al. |
| 6,210,435 | B1 | 4/2001 | Piplani et al. | 6,344,044 | B1 | 2/2002 | Fulkerson et al. |
| 6,214,038 | B1 | 4/2001 | Piplani et al. | 6,344,054 | B1 | 2/2002 | Parodi |
| 6,214,039 | B1 | 4/2001 | Banas et al. | 6,344,055 | B1 | 2/2002 | Shukov |
| 6,217,608 | B1 | 4/2001 | Penn et al. | 6,346,118 | B1 | 2/2002 | Baker et al. |
| 6,221,102 | B1 | 4/2001 | Baker et al. | 6,346,119 | B1 | 2/2002 | Kuwahara et al. |
| 6,224,609 | B1 | 5/2001 | Ressemann et al. | 6,348,065 | B1 | 2/2002 | Brown et al. |
| 6,231,562 | B1 | 5/2001 | Khosravi et al. | 6,350,277 | B1 | 2/2002 | Kocur |
| 6,235,050 | B1 | 5/2001 | Quiachon et al. | 6,352,553 | B1 | 3/2002 | Van der Burg et al. |
| 6,235,051 | B1 | 5/2001 | Murphy | 6,352,561 | B1 | 3/2002 | Leopold et al. |
| 6,238,432 | B1 | 5/2001 | Parodi | 6,355,055 | B1 | 3/2002 | Waksman et al. |
| 6,240,616 | B1 | 6/2001 | Yan | 6,355,056 | B1 | 3/2002 | Pnheiro |
| 6,241,759 | B1 | 6/2001 | Piplani et al. | 6,355,060 | B1 | 3/2002 | Lenker et al. |
| 6,245,097 | B1 | 6/2001 | Inoue | 6,355,063 | B1 | 3/2002 | Calcote |
| 6,245,099 | B1 | 6/2001 | Edwin et al. | 6,357,104 | B1 | 3/2002 | Myers |
| 6,245,100 | B1 | 6/2001 | Davila et al. | 6,358,276 | B1 | 3/2002 | Edwin et al. |
| 6,245,101 | B1 | 6/2001 | Drasler et al. | 6,358,284 | B1 | 3/2002 | Fearnot et al. |
| 6,245,102 | B1 | 6/2001 | Jayaraman | 6,361,637 | B2 | 3/2002 | Martin et al. |
| 6,248,116 | B1 | 6/2001 | Chevillon et al. | 6,363,938 | B2 | 4/2002 | Saadat |
| 6,251,132 | B1 | 6/2001 | Ravenscroft et al. | 6,364,856 | B1 | 4/2002 | Ding et al. |
| 6,251,136 | B1 | 6/2001 | Guruwaiya et al. | 6,364,904 | B1 | 4/2002 | Smith |
| 6,254,593 | B1 | 7/2001 | Wilson | 6,368,346 | B1 | 4/2002 | Jadhav |
| 6,254,632 | B1 | 7/2001 | Wu et al. | 6,368,347 | B1 | 4/2002 | Maini et al. |
| 6,258,073 | B1 | 7/2001 | Mauch | 6,368,355 | B1 | 4/2002 | Uflacker |
| 6,258,114 | B1 | 7/2001 | Konya et al. | 6,371,979 | B1 | 4/2002 | Beyar et al. |
| 6,258,116 | B1 | 7/2001 | Hojeibane | 6,372,136 | B1 | 4/2002 | Nakatsuka |
| 6,261,316 | B1 | 7/2001 | Shaolian et al. | 6,375,787 | B1 | 4/2002 | Lukic |
| 6,261,317 | B1 | 7/2001 | Inoue | 6,379,381 | B1 | 4/2002 | Hossainy et al. |
| 6,264,662 | B1 | 7/2001 | Lauterjung | 6,379,382 | B1 | 4/2002 | Yang |
| 6,264,684 | B1 | 7/2001 | Banas et al. | 6,379,392 | B1 | 4/2002 | Walak |
| 6,267,783 | B1 | 7/2001 | Letendre et al. | 6,383,213 | B2 | 5/2002 | Wilson et al. |
| 6,267,834 | B1 | 7/2001 | Shannon et al. | 6,383,214 | B1 | 5/2002 | Banas et al. |
| 6,270,524 | B1 | 8/2001 | Kim | 6,387,119 | B2 | 5/2002 | Wolf et al. |
| 6,270,525 | B1 | 8/2001 | Letendre et al. | 6,387,124 | B1 | 5/2002 | Buscemi et al. |
| 6,270,707 | B1 | 8/2001 | Hori et al. | 6,391,050 | B1 | 5/2002 | Broome |
| 6,273,909 | B1 | 8/2001 | Kugler et al. | 6,391,052 | B2 | 5/2002 | Buirge et al. |
| 6,273,910 | B1 | 8/2001 | Limon | 6,395,019 | B2 | 5/2002 | Chobotov |
| 6,273,911 | B1 | 8/2001 | Cox et al. | 6,395,022 | B1 | 5/2002 | Piplani et al. |
| 6,280,457 | B1 | 8/2001 | Wallace et al. | 6,395,208 | B1 | 5/2002 | Herweck et al. |
| 6,280,466 | B1 | 8/2001 | Kugler et al. | 6,398,803 | B1 | 6/2002 | Layne et al. |
| 6,280,467 | B1 | 8/2001 | Leonhardt et al. | 6,402,779 | B1 | 6/2002 | Colone et al. |
| 6,283,991 | B1 | 9/2001 | Cox et al. | 6,406,489 | B1 | 6/2002 | Richter et al. |
| 6,287,315 | B1 | 9/2001 | Wijeratne et al. | 6,409,749 | B1 | 6/2002 | Maynard |
| 6,287,329 | B1 | 9/2001 | Duarig et al. | 6,409,750 | B1 | 6/2002 | Hyodoh |
| 6,287,330 | B1 | 9/2001 | Johansson et al. | 6,409,754 | B1 | 6/2002 | Smith et al. |
| 6,287,335 | B1 | 9/2001 | Drasler et al. | 6,409,756 | B1 | 6/2002 | Murphy |
| 6,287,336 | B1 | 9/2001 | Globerman et al. | 6,409,757 | B1 | 6/2002 | Trout et al. |
| 6,290,728 | B1 | 9/2001 | Phelps et al. | 6,409,761 | B1 | 6/2002 | Jang |
| 6,293,966 | B1 | 9/2001 | Frantzen | 6,413,269 | B1 | 7/2002 | Bui et al. |
| 6,293,968 | B1 | 9/2001 | Taheri | 6,416,535 | B1 | 7/2002 | Lazarus |
| 6,293,969 | B1 | 9/2001 | Chuter | 6,416,536 | B1 | 7/2002 | Yee |
| 6,296,661 | B1 | 10/2001 | Davila et al. | 6,416,537 | B1 | 7/2002 | Martakos et al. |
| 6,302,891 | B1 | 10/2001 | Nadal | 6,416,538 | B1 | 7/2002 | Ley et al. |
| 6,302,905 | B1 | 10/2001 | Goldsteen et al. | 6,416,539 | B1 | 7/2002 | Hassdenteufel |
| 6,302,906 | B1 | 10/2001 | Goicoechea et al. | 6,416,542 | B1 | 7/2002 | Marcade et al. |
| 6,302,908 | B1 | 10/2001 | Parodi | 6,419,701 | B1 | 7/2002 | Cook et al. |
| 6,303,100 | B1 | 10/2001 | Ricci et al. | 6,423,084 | B1 | 7/2002 | St. Germain |
| 6,306,141 | B1 | 10/2001 | Jervis | 6,423,089 | B1 | 7/2002 | Gingras et al. |
| 6,306,145 | B1 | 10/2001 | Leschinsky | 6,423,090 | B1 | 7/2002 | Hancock |
| 6,306,164 | B1 | 10/2001 | Kujawski | 6,425,855 | B2 | 7/2002 | Tomonto |
| 6,306,165 | B1 | 10/2001 | Patnaik et al. | 6,425,898 | B1 | 7/2002 | Wilson et al. |
| 6,312,458 | B1 | 11/2001 | Golds | 6,428,506 | B1 | 8/2002 | Simhambhatla et al. |
| 6,312,460 | B2 | 11/2001 | Drasler et al. | 6,428,565 | B1 | 8/2002 | Wisselink |
| 6,312,462 | B1 | 11/2001 | McDermott et al. | 6,428,566 | B1 | 8/2002 | Holt |
| 6,315,791 | B1 | 11/2001 | Gingras et al. | 6,428,567 | B2 | 8/2002 | Wilson et al. |
| 6,319,276 | B1 | 11/2001 | Holman et al. | 6,428,569 | B1 | 8/2002 | Brown |
| 6,319,278 | B1 | 11/2001 | Quinn | 6,428,570 | B1 | 8/2002 | Globerman |
| 6,319,279 | B1 | 11/2001 | Shannon et al. | 6,428,571 | B1 | 8/2002 | Lentz et al. |
| 6,322,587 | B1 | 11/2001 | Quiachon et al. | 6,432,129 | B2 | 8/2002 | DiCaprio |
| 6,325,819 | B1 | 12/2001 | Pavcnik et al. | 6,432,131 | B1 | 8/2002 | Ravenscroft |
| 6,325,823 | B1 | 12/2001 | Horzewski et al. | 6,432,132 | B1 | 8/2002 | Cottone et al. |
| 6,325,824 | B2 | 12/2001 | Limon | 6,436,104 | B2 | 8/2002 | Hoieibane |
| 6,325,825 | B1 | 12/2001 | Kula et al. | 6,436,133 | B1 | 8/2002 | Furst et al. |
| 6,328,762 | B1 | 12/2001 | Anderson et al. | 6,436,134 | B2 | 8/2002 | Richter et al. |
| 6,331,186 | B1 | 12/2001 | Wang et al. | 6,436,135 | B1 | 8/2002 | Goldfarb |

| | | |
|---|---|---|
| 6,440,165 B1 | 8/2002 | Richter et al. |
| 6,443,941 B1 | 9/2002 | Slepian et al. |
| 6,443,979 B1 | 9/2002 | Stalker et al. |
| 6,443,981 B1 | 9/2002 | Colone et al. |
| 6,447,501 B1 | 9/2002 | Solar et al. |
| 6,447,522 B2 | 9/2002 | Gambale et al. |
| 6,451,047 B2 | 9/2002 | McCrea et al. |
| 6,451,050 B1 | 9/2002 | Rudakov et al. |
| 6,451,053 B1 | 9/2002 | Dehdashtian et al. |
| 6,454,796 B1 | 9/2002 | Barkman et al. |
| 6,461,381 B2 | 10/2002 | Israel et al. |
| 6,464,720 B2 | 10/2002 | Boatman et al. |
| 6,464,721 B1 | 10/2002 | Marcade et al. |
| 6,464,722 B2 | 10/2002 | Israel et al. |
| 6,471,718 B1 | 10/2002 | Staehle et al. |
| 6,471,720 B1 | 10/2002 | Ehr et al. |
| 6,471,721 B1 | 10/2002 | Dang |
| 6,471,722 B1 | 10/2002 | Inoue |
| 6,475,166 B1 | 11/2002 | Escano |
| 6,475,208 B2 | 11/2002 | Mauch |
| 6,475,236 B1 | 11/2002 | Roubin et al. |
| 6,475,237 B2 | 11/2002 | Drasler |
| 6,475,238 B1 | 11/2002 | Fedida |
| 6,475,466 B1 | 11/2002 | Ricci et al. |
| 6,478,807 B1 | 11/2002 | Foreman et al. |
| 6,478,815 B1 | 11/2002 | Alt |
| 6,478,816 B1 | 11/2002 | Kveen et al. |
| 6,482,227 B1 | 11/2002 | Solovay |
| 6,485,507 B1 | 11/2002 | Walak et al. |
| 6,485,508 B1 | 11/2002 | McGuinness |
| 6,485,509 B2 | 11/2002 | Killion et al. |
| 6,485,511 B2 | 11/2002 | Lau et al. |
| 6,485,513 B1 | 11/2002 | Fan |
| 6,485,515 B2 | 11/2002 | Strecker |
| 6,485,524 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,488,705 B2 | 12/2002 | Schmitt et al. |
| 6,491,718 B1 | 12/2002 | Ahmad |
| 6,491,719 B1 | 12/2002 | Fogary et al. |
| 6,494,875 B1 | 12/2002 | Mauch |
| 6,494,904 B1 | 12/2002 | Love |
| 6,494,907 B1 | 12/2002 | Bulver |
| 6,494,909 B2 | 12/2002 | Greenhalgh |
| 6,497,722 B1 | 12/2002 | Von Oepen et al. |
| 6,497,723 B1 | 12/2002 | Starck et al. |
| 6,500,202 B1 | 12/2002 | Shaolian et al. |
| 6,500,203 B1 | 12/2002 | Thompson et al. |
| 6,500,204 B1 | 12/2002 | Igaki |
| 6,500,532 B1 | 12/2002 | Ruefer et al. |
| 6,503,271 B2 | 1/2003 | Duerig et al. |
| 6,506,211 B1 | 1/2003 | Doran et al. |
| 6,508,833 B2 | 1/2003 | Pavcnik et al. |
| 6,508,834 B1 | 1/2003 | Pinchasik et al. |
| 6,514,281 B1 | 2/2003 | Blaeser et al. |
| 6,517,558 B2 | 2/2003 | Gittings et al. |
| 6,517,571 B1 | 2/2003 | Brauker et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,520,986 B2 | 2/2003 | Martin et al. |
| 6,524,334 B1 | 2/2003 | Thompson |
| 6,524,335 B1 | 2/2003 | Hartley et al. |
| 6,524,336 B1 | 2/2003 | Papazolgou et al. |
| 6,530,765 B1 | 3/2003 | Zdrahala et al. |
| 6,530,947 B1 | 3/2003 | Euteneuer et al. |
| 6,530,950 B1 | 3/2003 | Alvarado et al. |
| 6,533,806 B1 | 3/2003 | Sullivan et al. |
| 6,533,807 B2 | 3/2003 | Wolinsky et al. |
| 6,533,808 B1 | 3/2003 | Thompson et al. |
| 6,533,811 B1 | 3/2003 | Ryan et al. |
| 6,537,202 B1 | 3/2003 | Frantzen |
| 6,540,778 B1 | 4/2003 | Quiachon et al. |
| 6,540,780 B1 | 4/2003 | Zilla et al. |
| 6,547,813 B2 | 4/2003 | Stiger et al. |
| 6,547,814 B2 | 4/2003 | Edwin et al. |
| 6,547,815 B2 | 4/2003 | Myers |
| 6,547,817 B1 | 4/2003 | Fischell et al. |
| 6,548,013 B2 | 4/2003 | Kadavy et al. |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,558,415 B2 | 5/2003 | Thompson |
| 6,562,063 B1 | 5/2003 | Euteneuer et al. |
| 6,565,597 B1 | 5/2003 | Fearnot |
| 6,569,150 B2 | 5/2003 | Teague |
| 6,569,190 B2 | 5/2003 | Whalen, II et al. |
| 6,569,193 B1 | 5/2003 | Cox et al. |
| 6,572,649 B2 | 6/2003 | Berry et al. |
| 6,575,994 B1 | 6/2003 | Marin |
| 6,576,009 B2 | 6/2003 | Ryan et al. |
| 6,579,314 B1 | 6/2003 | Lombardi et al. |
| 6,582,458 B1 | 6/2003 | White et al. |
| 6,589,274 B2 | 7/2003 | Stiger et al. |
| 6,589,275 B1 | 7/2003 | Ivancev et al. |
| 6,592,614 B2 | 7/2003 | Lenker et al. |
| 6,602,269 B1 | 8/2003 | Wallace et al. |
| 6,602,280 B2 | 8/2003 | Chobotov |
| 6,602,283 B2 | 8/2003 | Doran et al. |
| 6,605,110 B2 | 8/2003 | Harrison |
| 6,607,551 B1 | 8/2003 | Sullivan et al. |
| 6,613,082 B2 | 9/2003 | Yang |
| 6,613,083 B2 | 9/2003 | Alt |
| 6,613,084 B2 | 9/2003 | Yang |
| 6,620,190 B1 | 9/2003 | Colone |
| 6,626,938 B1 | 9/2003 | Butaric et al. |
| 6,635,079 B2 | 10/2003 | Unsworth et al. |
| 6,645,240 B2 | 11/2003 | Yee |
| 6,652,554 B1 | 11/2003 | Wholey et al. |
| 6,652,570 B2 | 11/2003 | Smith et al. |
| 6,652,573 B2 | 11/2003 | von Oepen |
| 6,652,575 B2 | 11/2003 | Wang |
| 6,652,580 B1 | 11/2003 | Chutter |
| 6,656,215 B1 | 12/2003 | Yanez et al. |
| 6,656,506 B1 | 12/2003 | Wu et al. |
| 6,660,030 B2 | 12/2003 | Shaolian et al. |
| 6,663,662 B2 | 12/2003 | Pacetti et al. |
| 6,663,663 B2 | 12/2003 | Kim et al. |
| 6,663,664 B1 | 12/2003 | Pacetti |
| 6,663,665 B2 | 12/2003 | Shaolian et al. |
| 6,663,667 B2 | 12/2003 | Dehdashtian et al. |
| 6,669,720 B1 | 12/2003 | Pierce |
| 6,669,723 B2 | 12/2003 | Killion et al. |
| 6,669,724 B2 | 12/2003 | Park et al. |
| 6,673,102 B1 | 1/2004 | Vonesh et al. |
| 6,673,103 B1 | 1/2004 | Golds et al. |
| 6,673,106 B2 | 1/2004 | Mitelberg et al. |
| 6,673,107 B1 | 1/2004 | Brandt et al. |
| 6,676,667 B2 | 1/2004 | Mareiro et al. |
| 6,676,695 B2 | 1/2004 | Solem |
| 6,679,911 B2 | 1/2004 | Burgermeister |
| 6,685,736 B1 | 2/2004 | White et al. |
| 6,689,158 B2 | 2/2004 | White et al. |
| 6,689,159 B2 | 2/2004 | Hartigan et al. |
| 6,692,523 B2 | 2/2004 | Holman et al. |
| 6,694,983 B2 | 2/2004 | Wolf et al. |
| 6,695,833 B1 | 2/2004 | Frantzen |
| 6,695,875 B2 | 2/2004 | Stelter et al. |
| 6,695,877 B2 | 2/2004 | Brucker et al. |
| 6,696,666 B2 | 2/2004 | Merdan et al. |
| 6,699,274 B2 | 3/2004 | Stinson |
| 6,699,277 B1 | 3/2004 | Freidberg et al. |
| 6,702,847 B2 | 3/2004 | DiCarlo |
| 6,702,849 B1 | 3/2004 | Dutta et al. |
| 6,706,064 B1 | 3/2004 | Anson |
| 6,709,449 B2 | 3/2004 | Camrud et al. |
| 6,709,455 B1 | 3/2004 | Chouinard |
| 6,712,827 B2 | 3/2004 | Ellis et al. |
| 6,716,238 B2 | 4/2004 | Elliott |
| 6,716,239 B2 | 4/2004 | Sowinski |
| 6,719,783 B2 | 4/2004 | Lentz et al. |
| 6,726,712 B1 | 4/2004 | Raeder-Devens |
| 6,730,119 B1 | 5/2004 | Smalling |
| 6,733,521 B2 * | 5/2004 | Chobotov et al. ............ 623/1.12 |
| 6,736,839 B2 | 5/2004 | Cummings |

| | | |
|---|---|---|
| 6,740,111 B1 | 5/2004 | Lauterjung |
| 6,740,114 B2 | 5/2004 | Burgermeister |
| 6,740,115 B2 | 5/2004 | Lombardi |
| 6,743,210 B2 | 6/2004 | Hart et al. |
| 6,743,511 B2 | 6/2004 | Dittrich et al. |
| 6,746,890 B2 | 6/2004 | Gupta |
| 6,752,829 B2 | 6/2004 | Kocur et al. |
| 6,755,855 B2 | 6/2004 | Yurek et al. |
| 6,758,858 B2 | 7/2004 | McCrea et al. |
| 6,761,733 B2 * | 7/2004 | Chobotov et al. ............ 623/1.12 |
| 6,770,086 B1 | 8/2004 | Girton et al. |
| 6,770,087 B2 | 8/2004 | Layne et al. |
| 6,773,453 B2 | 8/2004 | Ravenscroft |
| 6,773,457 B2 | 8/2004 | Ivancev et al. |
| 6,776,604 B1 | 8/2004 | Chobotov et al. |
| 6,776,793 B2 | 8/2004 | Brown et al. |
| 6,786,920 B2 | 9/2004 | Shannon et al. |
| 6,790,227 B2 | 9/2004 | Burgermeister |
| 6,790,230 B2 | 9/2004 | Beyersdorf et al. |
| 6,793,672 B2 | 9/2004 | Khosravi et al. |
| 6,796,999 B2 | 9/2004 | Pinchasik |
| 6,802,849 B2 | 10/2004 | Blaeser et al. |
| 6,802,856 B2 | 10/2004 | Wilson |
| 6,814,753 B2 | 11/2004 | Schmitt |
| 6,818,013 B2 | 11/2004 | Mitelberg et al. |
| 6,821,292 B2 | 11/2004 | Pazienza et al. |
| 6,824,558 B2 | 11/2004 | Parodi |
| 6,827,726 B2 | 12/2004 | Parodi |
| 6,827,731 B2 | 12/2004 | Annstrong et al. |
| 6,827,735 B2 | 12/2004 | Greenberg |
| 6,827,737 B2 | 12/2004 | Hill et al. |
| 6,833,004 B2 | 12/2004 | Ishii et al. |
| 6,841,213 B2 | 1/2005 | Parsonage et al. |
| 6,843,802 B1 | 1/2005 | Villalobos et al. |
| 6,849,086 B2 | 2/2005 | Cragg |
| 6,858,035 B2 | 2/2005 | Whayne |
| 6,860,900 B2 | 3/2005 | Clerc et al. |
| 6,863,685 B2 | 3/2005 | Davila et al. |
| 6,869,443 B2 | 3/2005 | Buscemi et al. |
| 6,878,160 B2 | 4/2005 | Gilligan et al. |
| 6,878,161 B2 | 4/2005 | Lenker |
| 6,884,260 B2 | 4/2005 | Kugler et al. |
| 6,899,728 B1 | 5/2005 | Phillips et al. |
| 6,918,925 B2 | 7/2005 | Tehrani |
| 6,918,927 B2 | 7/2005 | Bates et al. |
| 6,923,827 B2 | 8/2005 | Campbell et al. |
| 6,926,732 B2 | 8/2005 | Derus et al. |
| 6,929,659 B2 | 8/2005 | Pinchuk |
| 6,929,709 B2 | 8/2005 | Smith |
| 6,939,370 B2 | 9/2005 | Hartley et al. |
| 6,939,374 B2 | 9/2005 | Banik et al. |
| 6,942,689 B2 | 9/2005 | Majercak |
| 6,945,989 B1 | 9/2005 | Rourke et al. |
| 6,945,992 B2 | 9/2005 | Goodson et al. |
| 6,949,120 B2 | 9/2005 | Kveen et al. |
| 6,962,602 B2 | 11/2005 | Vardi et al. |
| 6,962,603 B1 | 11/2005 | Brown |
| 6,964,677 B2 | 11/2005 | Osypka |
| 6,974,471 B2 | 12/2005 | Van Schie et al. |
| 6,974,472 B2 | 12/2005 | Hong et al. |
| 6,981,982 B2 | 1/2006 | Armstrong et al. |
| 6,989,026 B2 | 1/2006 | Richter et al. |
| 6,994,722 B2 | 2/2006 | DiCarlo |
| 6,997,945 B2 | 2/2006 | Germain |
| 6,998,060 B2 | 2/2006 | Tomonto |
| 7,001,407 B2 | 2/2006 | Hansen et al. |
| 7,001,419 B2 | 2/2006 | DiCaprio et al. |
| 7,001,431 B2 | 2/2006 | Bao et al. |
| 7,011,673 B2 | 3/2006 | Fischell et al. |
| 7,011,674 B2 | 3/2006 | Brenneman |
| 7,022,132 B2 | 4/2006 | Kocur |
| 7,022,135 B2 | 4/2006 | Zilla et al. |
| 7,033,389 B2 | 4/2006 | Sherry |
| 7,056,325 B1 | 6/2006 | Makower |
| 7,056,336 B2 | 6/2006 | Armstrong et al. |
| 7,056,412 B2 | 6/2006 | Henderson |
| 7,066,951 B2 | 6/2006 | Chobotov |
| 7,073,504 B2 | 7/2006 | Callister et al. |
| 7,081,129 B2 | 7/2006 | Chobotov |
| 7,081,132 B2 | 7/2006 | Cook |
| 7,083,642 B2 | 8/2006 | Sirhan et al. |
| 7,090,693 B1 | 8/2006 | Chobotov et al. |
| 7,094,255 B2 | 8/2006 | Penn et al. |
| 7,108,715 B2 | 9/2006 | Brown et al. |
| 7,115,140 B2 | 10/2006 | Stoltze et al. |
| 7,125,464 B2 | 10/2006 | Chobotov et al. |
| 7,128,754 B2 | 10/2006 | Bolduc |
| 7,128,755 B2 | 10/2006 | Su et al. |
| 7,147,455 B2 | 12/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,160,318 B2 | 1/2007 | Greenberg et al. |
| 7,166,125 B1 | 1/2007 | Baker et al. |
| 7,175,651 B2 | 2/2007 | Kerr |
| 7,175,652 B2 | 2/2007 | Cook et al. |
| 7,189,256 B2 | 3/2007 | Smith |
| 7,192,441 B2 | 3/2007 | Sherry |
| 7,223,280 B2 | 5/2007 | Anson et al. |
| 7,226,474 B2 | 6/2007 | Iancea et al. |
| 7,229,470 B2 | 6/2007 | Brown et al. |
| 7,232,459 B2 | 6/2007 | Greenberg |
| 7,244,242 B2 | 7/2007 | Freyman |
| 7,273,494 B2 | 9/2007 | Rolando et al. |
| 7,284,399 B1 | 10/2007 | Sisco |
| 7,294,147 B2 | 11/2007 | Hartley |
| 7,314,484 B2 | 1/2008 | Deem et al. |
| 7,338,518 B2 | 3/2008 | Chobotov |
| 7,351,256 B2 | 4/2008 | Hojeibane et al. |
| 7,425,219 B2 | 9/2008 | Quadri |
| 7,452,374 B2 | 11/2008 | Hain et al. |
| 7,465,270 B2 | 12/2008 | Li |
| 7,485,138 B2 | 2/2009 | Fearnot et al. |
| 7,491,230 B2 | 2/2009 | Holman et al. |
| 7,491,234 B2 | 2/2009 | Palasis et al. |
| 7,500,988 B1 | 3/2009 | Butaric et al. |
| 7,510,571 B2 | 3/2009 | Spiridigliozzi et al. |
| 7,520,890 B2 | 4/2009 | Phillips |
| 7,520,895 B2 | 4/2009 | Douglas et al. |
| 7,530,988 B2 | 5/2009 | Evans et al. |
| 7,550,004 B2 | 6/2009 | Bahler et al. |
| 7,550,005 B2 | 6/2009 | Bates et al. |
| 7,556,645 B2 | 7/2009 | Lashinski et al. |
| 7,591,843 B1 | 9/2009 | Escano |
| 7,597,710 B2 | 10/2009 | Obermiller |
| 2001/0014794 A1 | 8/2001 | Moll |
| 2001/0019659 A1 | 9/2001 | Hirai |
| 2001/0029349 A1 | 10/2001 | Leschinsky |
| 2001/0039445 A1 | 11/2001 | Hall et al. |
| 2001/0041928 A1 | 11/2001 | Pavcnik et al. |
| 2001/0044652 A1 | 11/2001 | Moore |
| 2001/0049534 A1 | 12/2001 | Lachat |
| 2002/0007193 A1 | 1/2002 | Tanner et al. |
| 2002/0011684 A1 | 1/2002 | Bahar et al. |
| 2002/0016626 A1 | 2/2002 | DiMatteo et al. |
| 2002/0029051 A1 | 3/2002 | Callister et al. |
| 2002/0032408 A1 | 3/2002 | Parker et al. |
| 2002/0040236 A1 | 4/2002 | Lau et al. |
| 2002/0040237 A1 | 4/2002 | Lentz et al. |
| 2002/0042644 A1 | 4/2002 | Greenhalgh |
| 2002/0045931 A1 | 4/2002 | Sogard et al. |
| 2002/0045933 A1 | 4/2002 | Jang |
| 2002/0045934 A1 | 4/2002 | Jang |
| 2002/0045935 A1 | 4/2002 | Jang |
| 2002/0049487 A1 | 4/2002 | Lootz et al. |
| 2002/0049490 A1 | 4/2002 | Pollock et al. |
| 2002/0049493 A1 | 4/2002 | Jang |
| 2002/0052627 A1 | 5/2002 | Boylan et al. |
| 2002/0052644 A1 | 5/2002 | Shaolin et al. |
| 2002/0052649 A1 | 5/2002 | Greenhalgh |
| 2002/0055768 A1 | 5/2002 | Hess et al. |
| 2002/0065552 A1 | 5/2002 | Jayaraman et al. |
| 2002/0072792 A1 | 6/2002 | Burgermeister et al. |
| 2002/0072793 A1 | 6/2002 | Rolando et al. |
| 2002/0076542 A1 | 6/2002 | Kramer et al. |
| 2002/0077692 A1 | 6/2002 | Besselink |
| 2002/0082680 A1 | 6/2002 | Stanley et al. |
| 2002/0082682 A1 | 6/2002 | Barclay et al. |

| | | | |
|---|---|---|---|
| 2002/0082685 A1 | 6/2002 | Sirhan et al. |
| 2002/0095208 A1 | 7/2002 | Gregorich et al. |
| 2002/0096252 A1 | 7/2002 | Lukic |
| 2002/0107561 A1 | 8/2002 | Pinheiro |
| 2002/0120321 A1 | 8/2002 | Gunderson et al. |
| 2002/0120327 A1 | 8/2002 | Cox et al. |
| 2002/0123790 A1 | 9/2002 | White et al. |
| 2002/0123791 A1 | 9/2002 | Harrison |
| 2002/0123796 A1 | 9/2002 | Majercak et al. |
| 2002/0143387 A1 | 10/2002 | Soetikno et al. |
| 2002/0147492 A1 | 10/2002 | Shokoohi et al. |
| 2002/0151953 A1 | 10/2002 | Chobotov et al. |
| 2002/0151956 A1 | 10/2002 | Chobotov et al. |
| 2002/0161376 A1 | 10/2002 | Barry et al. |
| 2002/0165603 A1 | 11/2002 | Thornton et al. |
| 2002/0169497 A1 | 11/2002 | Wholey et al. |
| 2002/0183826 A1 | 12/2002 | Dorn et al. |
| 2002/0183827 A1 | 12/2002 | Derus et al. |
| 2002/0188346 A1 | 12/2002 | Healy et al. |
| 2002/0188347 A1 | 12/2002 | Mathis |
| 2002/0193867 A1 | 12/2002 | Gladdish, Jr. et al. |
| 2002/0193872 A1 | 12/2002 | Trout et al. |
| 2002/0193873 A1 | 12/2002 | Brucker et al. |
| 2002/0198585 A1 | 12/2002 | Wisselink |
| 2002/0198587 A1 | 12/2002 | Greenberg et al. |
| 2003/0004560 A1* | 1/2003 | Chobotov et al. ............ 623/1.11 |
| 2003/0004565 A1 | 1/2003 | Harnek et al. |
| 2003/0009212 A1 | 1/2003 | Kerr |
| 2003/0014075 A1 | 1/2003 | Rosenbluth et al. |
| 2003/0040803 A1 | 2/2003 | Rioux et al. |
| 2003/0050684 A1 | 3/2003 | Abrams et al. |
| 2003/0068296 A1 | 4/2003 | Ricci et al. |
| 2003/0083736 A1 | 5/2003 | Brown et al. |
| 2003/0097170 A1 | 5/2003 | Friedrich et al. |
| 2003/0120263 A1 | 6/2003 | Ouriel et al. |
| 2003/0120331 A1 | 6/2003 | Chobotov et al. |
| 2003/0125797 A1 | 7/2003 | Chobotov |
| 2003/0135256 A1 | 7/2003 | Gallagher et al. |
| 2003/0135261 A1 | 7/2003 | Kugler et al. |
| 2003/0176912 A1 | 9/2003 | Chuter et al. |
| 2003/0191518 A1 | 10/2003 | Spiridigliozzi et al. |
| 2003/0204236 A1 | 10/2003 | Letort |
| 2003/0204244 A1 | 10/2003 | Stiger |
| 2003/0212449 A1 | 11/2003 | Cox |
| 2003/0220683 A1 | 11/2003 | Minasian |
| 2003/0225453 A1 | 12/2003 | Murch |
| 2004/0024446 A1 | 2/2004 | Smith |
| 2004/0034407 A1 | 2/2004 | Sherry |
| 2004/0044395 A1 | 3/2004 | Nelson |
| 2004/0049212 A1 | 3/2004 | Whayne |
| 2004/0049264 A1 | 3/2004 | Sowinski et al. |
| 2004/0093055 A1 | 5/2004 | Bartorelli et al. |
| 2004/0093064 A1 | 5/2004 | Bosma |
| 2004/0093068 A1 | 5/2004 | Bergen et al. |
| 2004/0093078 A1 | 5/2004 | Moll et al. |
| 2004/0098096 A1 | 5/2004 | Eton |
| 2004/0106974 A1 | 6/2004 | Greenberg et al. |
| 2004/0116997 A1 | 6/2004 | Taylor et al. |
| 2004/0138734 A1* | 7/2004 | Chobotov et al. ............ 623/1.11 |
| 2004/0162607 A1 | 8/2004 | Masroor |
| 2004/0167614 A1 | 8/2004 | Anson |
| 2004/0210304 A1 | 10/2004 | Seguin et al. |
| 2004/0215213 A1 | 10/2004 | Dolan |
| 2004/0220655 A1 | 11/2004 | Swanson et al. |
| 2004/0220664 A1 | 11/2004 | Chobotov |
| 2004/0254625 A1 | 12/2004 | Stephens |
| 2005/0033406 A1 | 2/2005 | Barnhart et al. |
| 2005/0049691 A1 | 3/2005 | Mercile et al. |
| 2005/0058920 A1 | 3/2005 | Tokarski et al. |
| 2005/0075715 A1 | 4/2005 | Borges et al. |
| 2005/0090804 A1 | 4/2005 | Chobotov et al. |
| 2005/0090901 A1 | 4/2005 | Studer |
| 2005/0158272 A1 | 7/2005 | Whirley et al. |
| 2005/0171593 A1 | 8/2005 | Whirley et al. |
| 2005/0177222 A1 | 8/2005 | Mead |
| 2005/0222669 A1 | 10/2005 | Purdy |
| 2005/0228484 A1 | 10/2005 | Stephens et al. |
| 2006/0009833 A1* | 1/2006 | Chobotov et al. ............ 623/1.11 |
| 2006/0020319 A1 | 1/2006 | Kim |
| 2006/0079952 A1 | 4/2006 | Kaplan et al. |
| 2006/0136047 A1 | 6/2006 | Obermiller et al. |
| 2006/0149364 A1 | 7/2006 | Walak et al. |
| 2006/0178732 A1 | 8/2006 | Chobotov et al. |
| 2006/0186143 A1 | 8/2006 | Argentine |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0233991 A1 | 10/2006 | Humphrey et al. |
| 2006/0287713 A1 | 12/2006 | Douglas et al. |
| 2006/0292206 A1 | 12/2006 | Kim et al. |
| 2007/0012396 A1 | 1/2007 | Chobotov et al. |
| 2007/0016281 A1 | 1/2007 | Melsheimer |
| 2007/0055347 A1 | 3/2007 | Arbefeuille |
| 2007/0112413 A1 | 5/2007 | Smith |
| 2007/0162106 A1 | 7/2007 | Evans et al. |
| 2007/0167901 A1 | 7/2007 | Herrig et al. |
| 2007/0203571 A1 | 8/2007 | Kaplan et al. |
| 2007/0219627 A1 | 9/2007 | Chu et al. |
| 2007/0239273 A1 | 10/2007 | Allen |
| 2007/0244539 A1 | 10/2007 | Lentz et al. |
| 2007/0276477 A1 | 11/2007 | Lee et al. |
| 2007/0282369 A1 | 12/2007 | Gilson et al. |
| 2008/0015687 A1 | 1/2008 | Lashinski et al. |
| 2008/0027529 A1 | 1/2008 | Hartley et al. |
| 2008/0051705 A1 | 2/2008 | Von Oepen et al. |
| 2008/0114441 A1 | 5/2008 | Rust |
| 2008/0114442 A1 | 5/2008 | Mitchell et al. |
| 2008/0114443 A1 | 5/2008 | Mitchell |
| 2008/0115678 A1 | 5/2008 | Weinberg |
| 2008/0172119 A1 | 7/2008 | Yamasaki et al. |
| 2008/0228255 A1 | 9/2008 | Rust |
| 2009/0036971 A1 | 2/2009 | Humphrey et al. |
| 2009/0042796 A1 | 2/2009 | Wallach et al. |
| 2009/0082841 A1 | 3/2009 | Zacharias et al. |
| 2009/0082842 A1 | 3/2009 | Glynn |
| 2009/0082845 A1 | 3/2009 | Chobotov et al. |
| 2009/0082846 A1 | 3/2009 | Chobotov et al. |
| 2009/0082847 A1 | 3/2009 | Zacharias et al. |
| 2009/0092844 A1 | 4/2009 | Ware et al. |
| 2009/0099649 A1 | 4/2009 | Chobotov et al. |
| 2009/0132020 A1 | 5/2009 | Watson |
| 2009/0132026 A1 | 5/2009 | Martin et al. |
| 2009/0171431 A1 | 7/2009 | Swanson et al. |
| 2009/0182406 A1 | 7/2009 | Eidenschink |
| 2009/0198267 A1 | 8/2009 | Evans et al. |
| 2009/0287145 A1 | 11/2009 | Cragg et al. |
| 2010/0211052 A1 | 8/2010 | Brown et al. |
| 2010/0331958 A1 | 12/2010 | Chobotov et al. |
| 2011/0218609 A1 | 9/2011 | Chobotov et al. |

FOREIGN PATENT DOCUMENTS

| | | |
|---|---|---|
| EP | 0714641 | 6/1996 |
| EP | 0775472 | 5/1997 |
| EP | 0792627 | 9/1997 |
| EP | 0808613 | 11/1997 |
| EP | 0819411 | 1/1998 |
| EP | 0943302 | 9/1999 |
| EP | 0997115 | 5/2000 |
| EP | 0480667 | 4/2001 |
| EP | 1093772 | 4/2001 |
| EP | 1138280 | 10/2001 |
| EP | 0808140 | 12/2001 |
| EP | 1163991 | 12/2001 |
| EP | 1212991 | 6/2002 |
| EP | 1266636 | 12/2002 |
| EP | 1380270 | 1/2004 |
| EP | 1415617 | 4/2004 |
| JP | 49 042773 | 4/1974 |
| JP | 3109404 | 5/1991 |
| JP | 5161665 | 6/1993 |
| JP | 6100054 | 4/1994 |
| JP | 09117511 | 5/1997 |
| JP | 18-126862 | 6/2006 |
| JP | 18-136382 | 6/2006 |
| RU | 2029527 | 2/1995 |
| SU | 1217402 | 3/1986 |
| SU | 1237201 | 6/1986 |
| SU | 1237202 | 6/1986 |

| | | |
|---|---|---|
| SU | 1273077 | 11/1986 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |
| SU | 1732964 | 5/1992 |
| SU | 1768154 | 10/1992 |
| SU | 1812980 | 4/1993 |
| WO | WO 91/00792 | 1/1991 |
| WO | WO 92/22604 | 12/1992 |
| WO | WO 93/13824 | 7/1993 |
| WO | WO 93/19804 | 10/1993 |
| WO | WO 94/03127 | 2/1994 |
| WO | WO 95/03754 | 2/1995 |
| WO | WO 95/09586 | 4/1995 |
| WO | WO 96/14095 | 5/1996 |
| WO | WO 96/14808 | 5/1996 |
| WO | WO 97/07751 | 3/1997 |
| WO | WO 97/29716 | 8/1997 |
| WO | WO 98/06355 | 2/1998 |
| WO | WO 98/38947 | 9/1998 |
| WO | WO 98/41167 | 9/1998 |
| WO | WO 98/44870 | 10/1998 |
| WO | WO 98/44873 | 10/1998 |
| WO | WO 99/00073 | 1/1999 |
| WO | WO 99/26559 | 6/1999 |
| WO | WO 99/38455 | 8/1999 |
| WO | WO 99/43378 | 9/1999 |
| WO | WO 99/43379 | 9/1999 |
| WO | WO 00/10487 | 3/2000 |
| WO | WO 00/13613 | 3/2000 |
| WO | WO 00/42947 | 7/2000 |
| WO | WO 00/42948 | 7/2000 |
| WO | WO 00/44808 | 8/2000 |
| WO | WO 00/51522 | 9/2000 |
| WO | WO 00/67675 | 11/2000 |
| WO | WO 00/71179 | 11/2000 |
| WO | WO 01/05331 | 1/2001 |
| WO | WO 01/08599 | 2/2001 |
| WO | WO 01/15633 | 3/2001 |
| WO | WO 01/21108 | 3/2001 |
| WO | WO 01/30270 | 5/2001 |
| WO | WO 01/41675 | 6/2001 |
| WO | WO 01/56500 | 8/2001 |
| WO | WO 01/56504 | 8/2001 |
| WO | WO 01/58384 | 8/2001 |
| WO | WO 01/58387 | 8/2001 |
| WO | WO 01/66037 | 9/2001 |
| WO | WO 01/67993 | 9/2001 |
| WO | WO 01/74270 | 10/2001 |
| WO | WO 01/82836 | 11/2001 |
| WO | WO 02/36332 | 5/2002 |
| WO | WO 02/41804 | 5/2002 |
| WO | WO 02/078569 | 10/2002 |
| WO | WO 02/083038 | 10/2002 |
| WO | WO 02/100454 | 12/2002 |
| WO | WO 03/022180 | 3/2003 |
| WO | WO 03/053287 | 7/2003 |
| WO | WO 03/094795 | 11/2003 |
| WO | WO 03/094799 | 11/2003 |
| WO | WO 2004/002370 | 1/2004 |
| WO | WO 2004/002371 | 1/2004 |
| WO | WO 2004/017866 | 3/2004 |
| WO | WO 2004/078065 | 9/2004 |
| WO | WO 2009/042796 | 4/2009 |
| WO | WO 2009/086200 | 7/2009 |

OTHER PUBLICATIONS

The AneuRx® Stent Graft System Treatment for AAA brochure, "An Innovative Modular Approach for the Treatment of Abdominal Aortic Aneurysms (AAA)," Medtronic Ave, Inc. 1999.
The AneuRx® Stent Graft Treatment for TAA brochure, "An Endoluminal Solution for the Treatment of Descending Thoracic Aortic Aneurysms," Medtronic, Inc. 1999.
Blum et al. "Abdominal aortic aneurysms: preliminary technical and clinical results with transfemoral placement of endovascular self-expanding stent-grafts" Radiology 198(1):25-31 (1996). ;198(1):25-31 (1996).
Blum et al. "Endoluminal stent-grafts for infrarenal abdominal aortic aneurysms" N Engl J Med 336(1):13-20 (1997). ;336(1):13-20 (1997).
Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.
Canero et al., "Optimal stent implantation: three-dimensional evaluation of the mutual position of stent and vessel via intracoronary echocardiography," Computers in Cardiology, 261-264 (Sep. 1999).
Cooley, Denton A., Surgical Treatment of Aortic Aneurysms (Book), W.B. Saunders Company, West Washington Square, PA (1986).
Donayre, et al., "Fillable endovascular aneurysm repair", Endovascular Today, p. 64-66, Jan. 2009.
Dumoulin C. et al., "Mechanical behavior modeling of balloon expandable stents." Journal of Biomechanics, vol. 33, No. 11, pp. 1461-1470 (available online: Sep. 8, 2000).
Elger et al. "The Influence of Shape on the Stresses in Model Abdominal Aortic Aneurysms," Transactions of the ASME 326:326-32 (1996).
Ernst "Current therapy for infrarenal aortic aneurysms" N Engl J Med 336(1):58-60 (1997).
Haimovitch, L. and Patierson, N., "Robust growth is forecast for endovascular repair of AAAs," The BBI Newsletter, vol. 26, No. 5, pp. 113-144, (May 2003).
How et al. "Mechanical Properties of Arteries and Arterial Grafts," Chapter 1 of Cardiovascular Biomaterials Hasting, G.W. (ed.) London; New York: Springer-Verlag, 1992 pp. 1-35.
International Search Report and Written Opinion mailed on Mar. 26, 2009 for International Application No. PCT/US2008/077727 filed on Sep. 25, 2008 and published as WO/2009/042792 on Apr. 2, 2009.
Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 pages (1998).
Mandai, S. et al. (1992). "Direct Thrombosis of Aneurysms with Cellulose Acetate Polymer. Part I: Results of Thrombosis in Experimental Aneurysms," J. Neurosurgery 77:497-500.
Mirich et al., "Percutaneously Placed Endovascular Grafts for Aortic Aneurysms: Feasibility Study", Radiology, 170/3:1033-1037 (1989); 1033-1037 (1989).
Moore et al. "Transfemoral endovascular repair of abdominal aortic aneurysm: results of the North American EVT phase 1 trial" J Vasc Surg 23(4):543-553 (1996). ;23(4):543-553 (1996).
Mower et al. "Stress Distributions in Vascular Aneurysms: Factors Affecting Risk of Aneurysm Rupture," J. Surgical Research 55:151-61 (1993).
Parodi "Endovascular repair of abdominal aortic aneurysms and other arterial lesions" J Vasc Surg 21(4):549-557 (1995).;21(4):549-557 (1995).
Parodi et al., "Transfemoral intraluminal graft implantation for abdominal aortic aneurysms," Ann. Vasc. Surg., 5(6):491-499 (1991).
Perry, M. D. and Chang, R. T., "Finite Element Analysis of NI-TI Alloy Stent Deployment," Proceedings of the Second International Conference on SMST, Asilomar Conference Center, Pacific Grove CA. USA (1997).
Rogers et al., "Balloon-Artery Interactions During Stent Placement: A finite element analysis approach to pressure, compliance and stent design as contributors to vascular injury", 1999 American Heart Association pp. 378-383.
Stern et al., "Interactive Definition of Endoluminal Aortic Stent Size and Morphology Based on Virtual Angioscopic Rendering of 3D Magnetic Resonance Angiography (MRA)," Cars. Computer Assisted Radiology and Surgery, Proceedings of the International Symposium on Computer Assisted Radiology and Surgery:176-180 (Jun. 1999).
Uflacker, R. and Robinson, J., "Endovascular treatment of abdominal aortic aneurysms: a review," Eur. Radial.,11:739-753 (2001).

Verhagen "Latest AAA Innovations: The Endurant Stent Graft System", Veith Symposium Nov. 17, 2007.
Verhagen, Hence J.M. "Endurant Medtronic Endograft for EVAR: advantages & early experience", Slides from Veith Symposium Presentation Nov. 22, 2008.
Vos, A.F.W. et al., "Endovascular Grafting of Complex Aortic Aneurysms with a modular site Branch Stent Graft System in a Porcine Model", Eur J Vasc Endovasc Surg, May 2004 vol. 27 492-497.
Volodos, N.L. et al. (1987). "New Balloon Catheter for Dilating Arteries and Installing Prosthesis During Distal Endoprosthetics With Self-Fixing Synthetic Prosthesis," *Thesis of VIII Symposium* (Oct. 8-10, 1987), Abstract Only in English, four pages.
Volodos, N.L. et al. (1986) "Self-Fixing Synthetic Prostheisis for Endoprosthesis of Vessels," Vestnik Khigurgii pp. 123-124, Abstract Only in English.
Volodos, N.L. et al. (1989). "Clinical Experience in Use of Self-Fixing Synthetic Prosthesis for Distal and Intraoperative Endoprosthestics of Aora and Iliac Arteries," Theses of Ixth All-Union Symposium (Oct. 2-3, 1989), Abstract only in English, four pages.
Web page, "Drug Eluting Stents—Why Use Drug Eluting Stents?" Polymer Coatings Division; at: URLhttp://www.lombardmedlcal.co.uk/lombard/pcde.why.html; Lombard Medical; printed Feb. 1, 2005.
Whitcher, "Simulation of in vivo loading conditions of nitinol vascular stent structures", 1997, Elsevier Science Ltd., pp. 1005-1011.
Whitcher, F., "A Finite Element Treatment of the In-Vivo Loading Conditions of NITI AD Vascular Stent and Graft Structures," Proceedings of the Second International Conference on SMST, Asilomar Conference Center, Pacific Grove. CA, USA (1997).
Wisselink, W. et al. (2001). "Clipping of Inferior Mesenteric and Lumbar Arteries via Retroperitoneal Laparo-Endoscopic Approach as a Treatment of Persistent Endoleak" Chapter 18 in Endoleaks and Endotension, Veith, F.J. et al. eds. Marcel Dekker, Inc. pp. 211-220.
Extended European Search Report Mailed Dec. 16, 2009 in European Application No. 09175398.8 filed: Oct. 15, 2004 and published as: EP 2145607 on Jan. 20, 2010.
International Preliminary Report on Patentability mailed on Apr. 15, 2010 for International Application No. PCT/US2008/078846 filed on Oct. 3, 2008 and published as WO/2009/046372 on Apr. 9, 2009.
International Search Report and Written Opinion mailed on Jul. 30, 2009 for International Application No. PCT/US2008/078846 filed on Oct. 3, 2008 and published as WO/2009/046372 on Apr. 9, 2009.
International Preliminary Report on Patentability mailed on Apr. 8, 2010 for International Application No. PCT/US2008/077714 filed on Sep. 25, 2008 and published as WO/2009/042789 on Apr. 2, 2009.
International Search Report and Written Opinion mailed on: May 1, 2009 for International Application No. PCT/US2008/077714 filed on Sep. 25, 2008 and published as WO/2009/042789 on Apr. 2, 2009.
International Preliminary Report on Patentability mailed on May 27, 2010 for International Application No. PCT/US2008/083451 filed on Nov. 13, 2008 and published as WO/2009/064923 on May 22, 2009.
International Search Report and Written Opinion mailed on Jun. 30, 2009 for International Application No. PCT/US2008/083451 filed on Nov. 13, 2008 and published as WO/2009/064923 on May 22, 2009.
International Search Report and Written Opinion mailed on Mar. 26, 2009 for International Application No. PCT/US2008/077727 filed on Sep. 25, 2008 and published as WO2009/042796 on Apr. 2, 2009.

International Preliminary Report on Patentability mailed on Apr. 8, 2010 for International Application No. PCT/US2008/077727 filed on Sep. 25, 2008 and published as WO2009/042796 on Apr. 2, 2009.
Office Action mailed: Jan. 14, 2010 in U.S. Appl. No. 11/861,739, filed Sep. 26, 2007 and published as: US2009/0082841 on Mar. 26, 2009.
Office Action Response mailed Jun. 14, 2010 in U.S. Appl. No. 11/861,739, filed Sep. 26, 2007 and published as: US2009/0082841 on Mar. 26, 2009.
Office Action mailed: Apr. 1, 2010 in U.S. Appl. No. 11/861,756, filed Sep. 26, 2007 and published as: US2009/0082842 on Mar. 26, 2009.
Office Action Response mailed: Jan. 4, 2010 in U.S. Appl. No. 11/861,731, filed Sep. 26, 2007 and published as: US2009/0082847 on Mar. 26, 2009.
Office Action mailed: Apr. 14, 2010 in U.S. Appl. No. 11/861,731, filed Sep. 26, 2007 and published as: US2009/0082847 on Mar. 26, 2009.
Extended European Search Report Mailed Jul. 27, 2010 in European Application No. 10005904.7 filed: Apr. 11, 2002 and published as: EP 2221023 on Aug. 25, 2010.
Office Action mailed: Aug. 26, 2010 in U.S. Appl. No. 11/861,739, filed Sep. 26, 2007 and published as: US2009/0082841 on Mar. 26, 2009.
Office Action Response mailed: Sep. 1, 2010 in U.S. Appl. No. 11/861,756, filed Sep. 26, 2007 and published as: US2009/0082842 on Mar. 26, 2009.
Office Action mailed: Oct. 6, 2010 in U.S. Appl. No. 11/861,756, filed Sep. 26, 2007 and published as: US2009/0082842 on Mar. 26, 2009.
Office Action mailed: Nov. 23, 2010 in U.S. Appl. No. 11/861,731, filed Sep. 26, 2007 and published as: US2009/0082847 on Mar. 26, 2009.
International Preliminary Report on Patentability mailed on Jul. 1, 2010 for International Application No. PCT/US2008/087831 filed on Dec. 19, 2008 and published as WO/2009/086200 on Jul. 9, 2009.
International Search Report and Written Opinion mailed on May 28, 2009 for International Application No. PCT/US2008/087831 filed on Dec. 19, 2008 and published as WO/2009/086200 on Jul. 9, 2009.
Office Action mailed on: May 3, 2011 in U.S. Appl. No. 11/941,450, filed Nov. 16, 2007 and published as: 2009/0132020 on: May 21, 2009.
Office Action mailed on: Dec. 9, 2010 in U.S. Appl. No. 11/941,450, filed Nov. 16, 2007 and published as: 2009/0132020 on: May 21, 2009.
Office Action Response mailed on: Sep. 10, 2010 in U.S. Appl. No. 11/941,450, filed Nov. 16, 2007 and published as: 2009/0132020 on: May 21, 2009.
Office Action mailed on: Mar. 15, 2010 in U.S. Appl. No. 11/941,450, filed Nov. 16, 2007 and published as: 2009/0132020 on: May 21, 2009.
Office Action Response mailed on: Nov. 20, 2009 in U.S. Appl. No. 11/941,450, filed Nov. 16, 2007 and published as: 2009/0132020 on: May 21, 2009.
Office Action mailed on: Oct. 22, 2009 in U.S. Appl. No. 11/941,450, filed Nov. 16, 2007 and published as: 2009/0132020 on: May 21, 2009.

\* cited by examiner

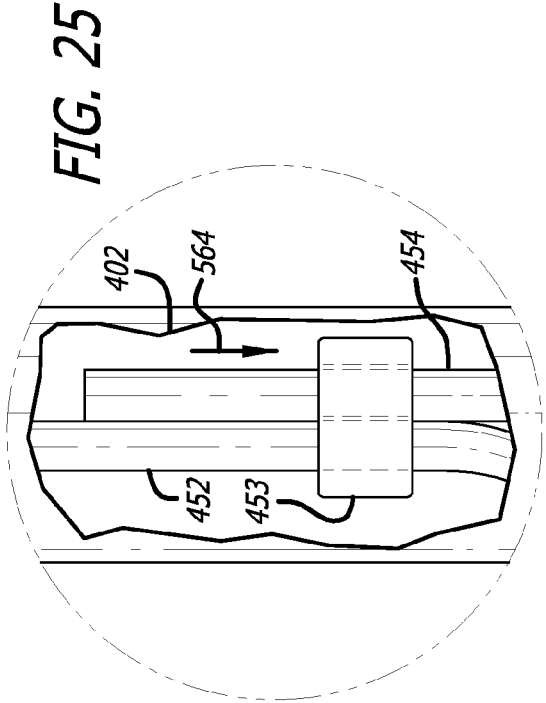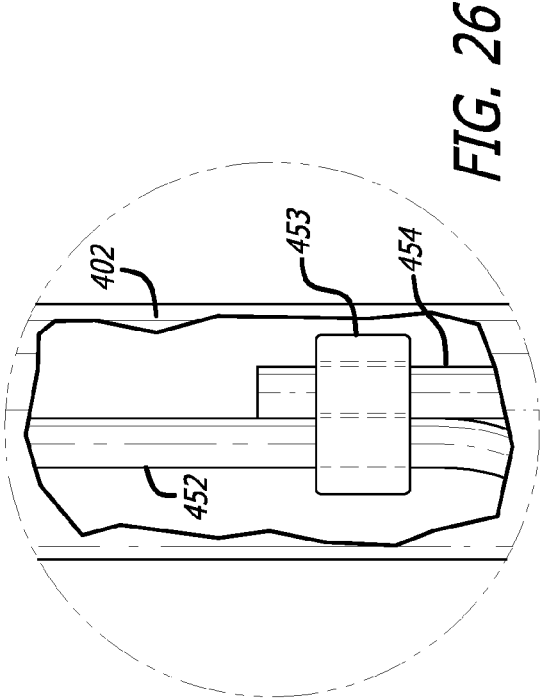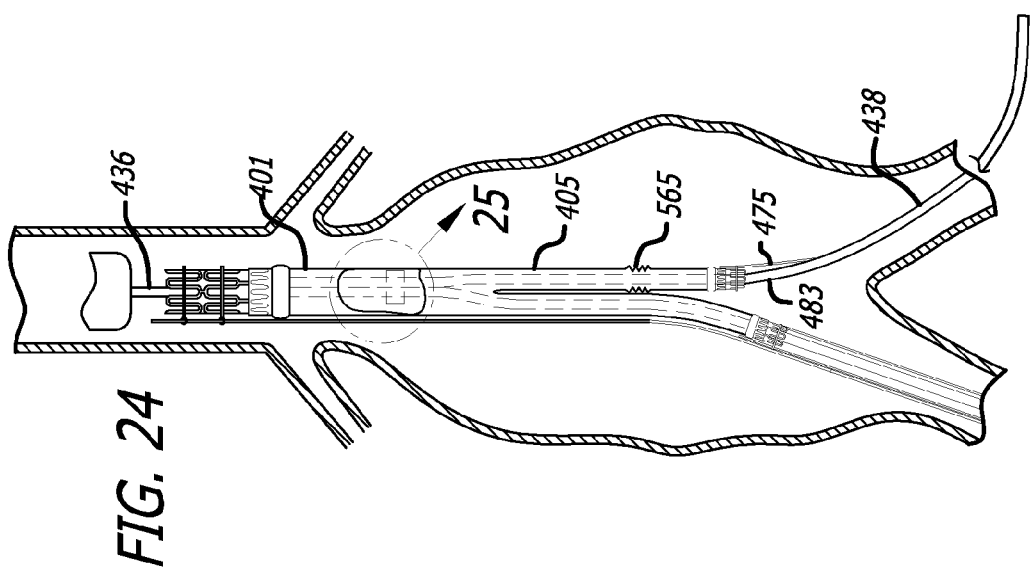

DELIVERY SYSTEM AND METHOD FOR BIFURCATED GRAFT

BACKGROUND OF THE INVENTION

The present invention relates generally to a system and method for the treatment of disorders of the vasculature. More specifically, a system and method for treatment of an abdominal aortic aneurysm and the like, which is a condition manifested by expansion and weakening of the aorta. Prior methods of treating aneurysms have consisted of invasive surgical methods with graft placement within the affected vessel as a reinforcing member of the artery. However, such a procedure requires a surgical cut down to access the vessel, which in turn can result in a catastrophic rupture of the aneurysm due to the decreased external pressure from the surrounding organs and tissues, which are moved during the procedure to gain access to the vessel. Accordingly, surgical procedures can have a high mortality rate due to the possibility of the rupture discussed above in addition to other factors. Other risk factors for surgical treatment of aortic aneurysms can include poor physical condition of the patient due to blood loss, anuria, and low blood pressure associated with the aortic abdominal aneurysm.

Due to the inherent risks and complexities of surgical intervention, various attempts have been made to develop alternative methods for deployment of grafts within aortic aneurysms. One such method is the non-invasive technique of percutaneous delivery by a catheter-based system.

U.S. Patent Application Publication No. US 2004/0138734, which is incorporated herein in its entirety by reference, describes systems and methods for the delivery of endovascular grafts, including bifurcated grafts. FIG. 1 illustrates a delivery system 10 of such publication for delivery and deployment of a bifurcated intracorporeal device 12 within a patient's body. The delivery system 10 includes an elongate shaft 14 having a proximal section and a distal section. The bifurcated intracorporeal device 12 is disposed on the distal section of the elongate shaft 14. The distal section of the elongate shaft 14 also includes an elongate primary belt support member 16 and at least one primary belt 18 secured to the primary belt support member 16. The primary belt 18 is configured to be circumferentially disposed about a primary portion 15 of the bifurcated intracorporeal device 12 to constrain such portion 15 of the device 12. A primary release member 20 engages and releasably secures the primary belt 18 in the constraining configuration. The distal section of the elongate shaft 14 also includes at least one elongate secondary belt support member 22 disposed adjacent the elongate primary belt support member 16. At least one secondary belt 24 is secured to the secondary belt support member 22 and is configured to be circumferentially disposed about a secondary leg portion 23 of the bifurcated intracorporeal device 12 to constrain such portion 23 of the device 12. A secondary release member 26 engages and releasably secures the secondary belt 24 in a constraining configuration.

The distal end of the delivery system 10 is introduced into the patient's body and advanced to a desired site within the patient's body. The delivery system 10 generally delivers the bifurcated intracorporeal device 12 via a single patient lumen or vessel, for example, either the left or right iliac (or femoral) artery. After the delivery system has been positioned above the carina of the iliac artery bifurcation, the secondary belt support member 22, and thereby the secondary leg portion 23, is moved laterally to align with the other of the iliac arteries. To facilitate such, a release strand 28, comprising first and second strands 27 and 29, is looped through a proximal portion of the secondary support member 22. The distal ends of the strands 27 and 29 are interconnected at an actuator hub 30 while the opposed proximal ends of strands 27 and 29 are directed out a secondary opening from the other of the iliac (femoral) arteries. As shown in FIG. 1, the secondary release member 26 is also attached to the actuator hub 30. When both strands 27 and 29 are pulled equally, they can be utilized to pull the secondary support member 22, but they do not cause any relative movement to the secondary release member 26 since the strands 27 and 29 apply an equal force to the actuator hub 30. To release the secondary belt 24, strand 29 is pulled proximally such that the actuator hub 30, and thereby the secondary release member 26, will be pulled proximally until the secondary release member releases the secondary belt 24.

To assist in directing of the strands 27 and 29 of the release strand 28 toward the secondary opening in the other of the arteries, the release strand 28 may initially be covered by a tube 32 or sheath or the like. During initial delivery of the delivery system 10, the tube 32 may either be fished, directed along a guide wire, or otherwise directed through the secondary opening. After the tube 32 is directed through the secondary opening, the tube 32 is removed from the release strand 28 such that both strands 27 and 29 are exposed.

SUMMARY OF THE INVENTION

In one aspect, the present invention may provide a delivery system for a bifurcated or modular intracorporeal device. The delivery system comprises a shaft having a distal section supporting a primary support member positioned to be disposed within at least a primary portion of the bifurcated or modular intracorporeal device and a secondary support member disposed adjacent the primary support member and extending within a secondary portion of the bifurcated or modular intracorporeal device. At least one belt is configured to be circumferentially disposed about a portion of the secondary support member so to at least partially constrain the secondary portion of the bifurcated or modular intracorporeal device. A tube defining a lumen is secured relative to the secondary support member. A release member is configured to engage and releasably secure the belt in a constraining configuration. The release member extends through at least a portion of the tube lumen such that the release member is accessible adjacent a proximal end of the tube.

In another aspect, the invention may provide a method of delivering a bifurcated or modular graft having a main body portion, an ipsilateral leg and a contralateral leg. The method comprises positioning a distal end of a shaft into a target vessel through a first access hole with the distal end of the shaft supporting a primary support member disposed within the main body portion and ipsilateral leg and a secondary support member disposed adjacent the contralateral leg; extending a proximal end of a tube out through a second access hole, a distal end of the tube secured relative to the secondary support member, the tube defining a lumen extending therein; releasing a primary belt configured to be circumferentially disposed about the primary support member to constrain at least a portion of the main body by proximally displacing a primary release member through the first access hole; accessing, through the tube lumen at the proximal end of the tube, a secondary release member configured to engage and releasably secure a secondary belt in a constraining configuration about the contralateral leg to constrain at least a portion thereof; and releasing the secondary belt by proximally displacing the primary release member.

BRIEF DESCRIPTION OF THE DRAWINGS

FIG. 3A is a cross-sectional view along the line 3A-3A in FIG. 3.

FIG. 3B is a cross-sectional view along the line 3B-3B in FIG. 3.

FIG. 3C is a cross-sectional view similar to FIG. 3B illustrating the access opening with the cover removed.

FIGS. 17-28 illustrate the magnified view of the abdominal aorta of the patient shown in FIG. 15 and depict a deployment sequence of a bifurcated endovascular stent graft with the delivery system of FIG. 2.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

As used herein, the proximal end of the elongate shaft is the end proximal to an operator of the delivery system 410 during use. The distal end of the elongate shaft is the end that enters and extends into the patient's body. The proximal and distal directions for the delivery system and endovascular graft loaded within the delivery system as used herein are the same. This convention is used throughout the specification for the purposes of clarity, although other conventions are commonly used. For example, another useful convention defines the proximal end of an endovascular graft as that end of the graft that is proximal to the source of blood flow going into the graft.

Figure 1:
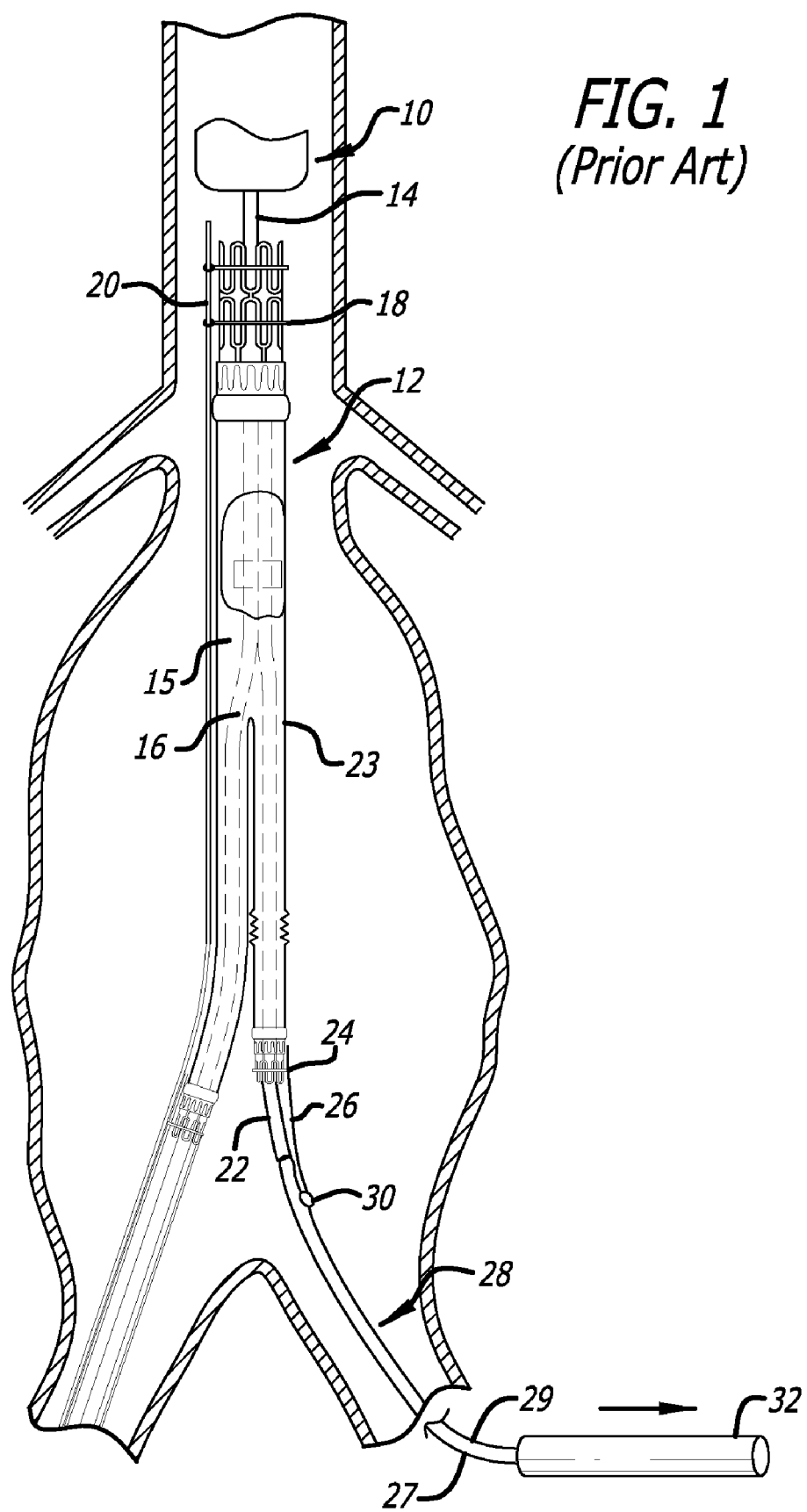
FIG. 1 is a magnified view of the abdominal aorta area of the patient with a prior art bifurcated endovascular stent graft delivery system illustrated therein.
Figure 2:
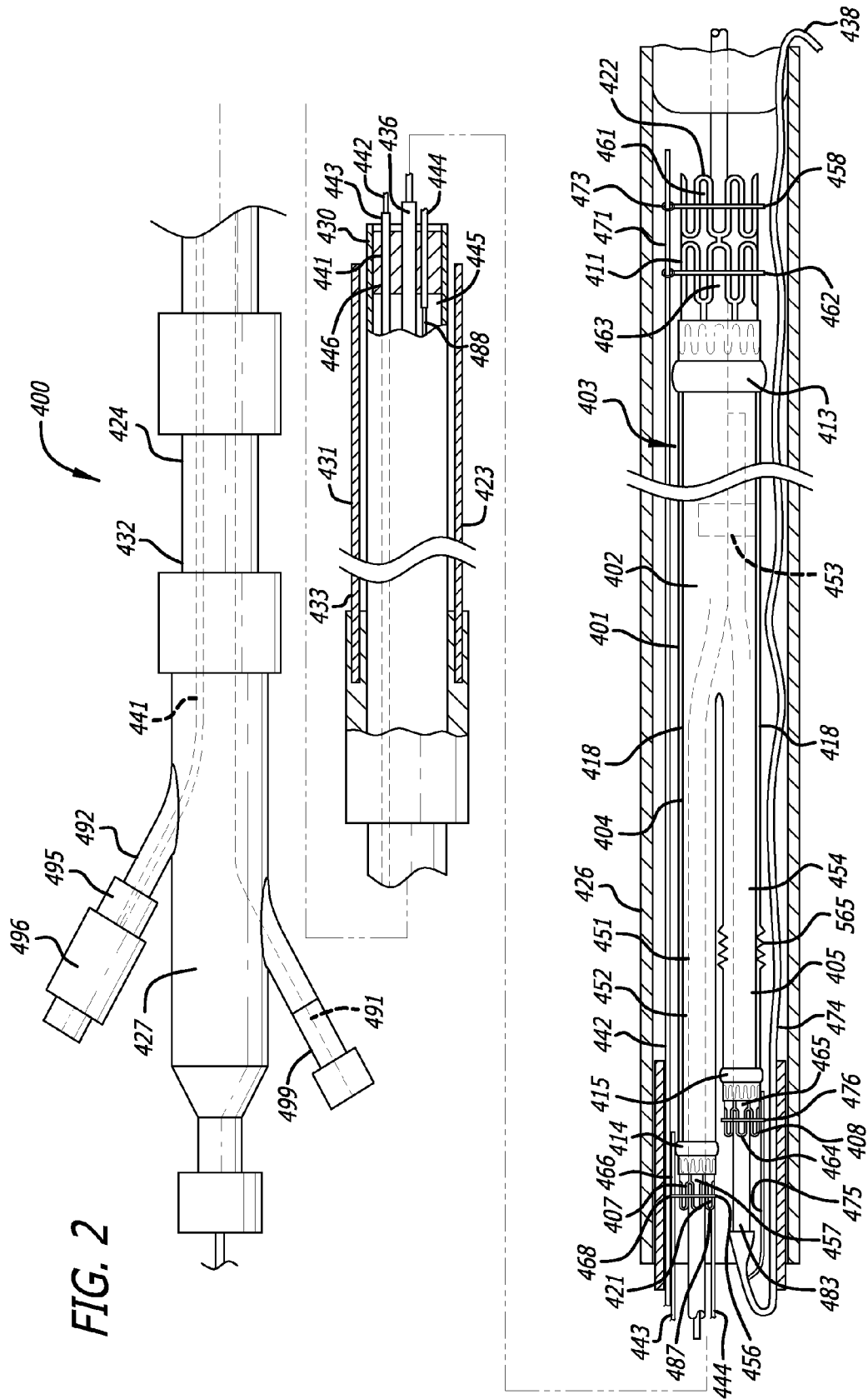
FIG. 2 is an elevational view in partial section of an embodiment of a delivery system in accordance with one or more aspects of the invention.
Figure 3:
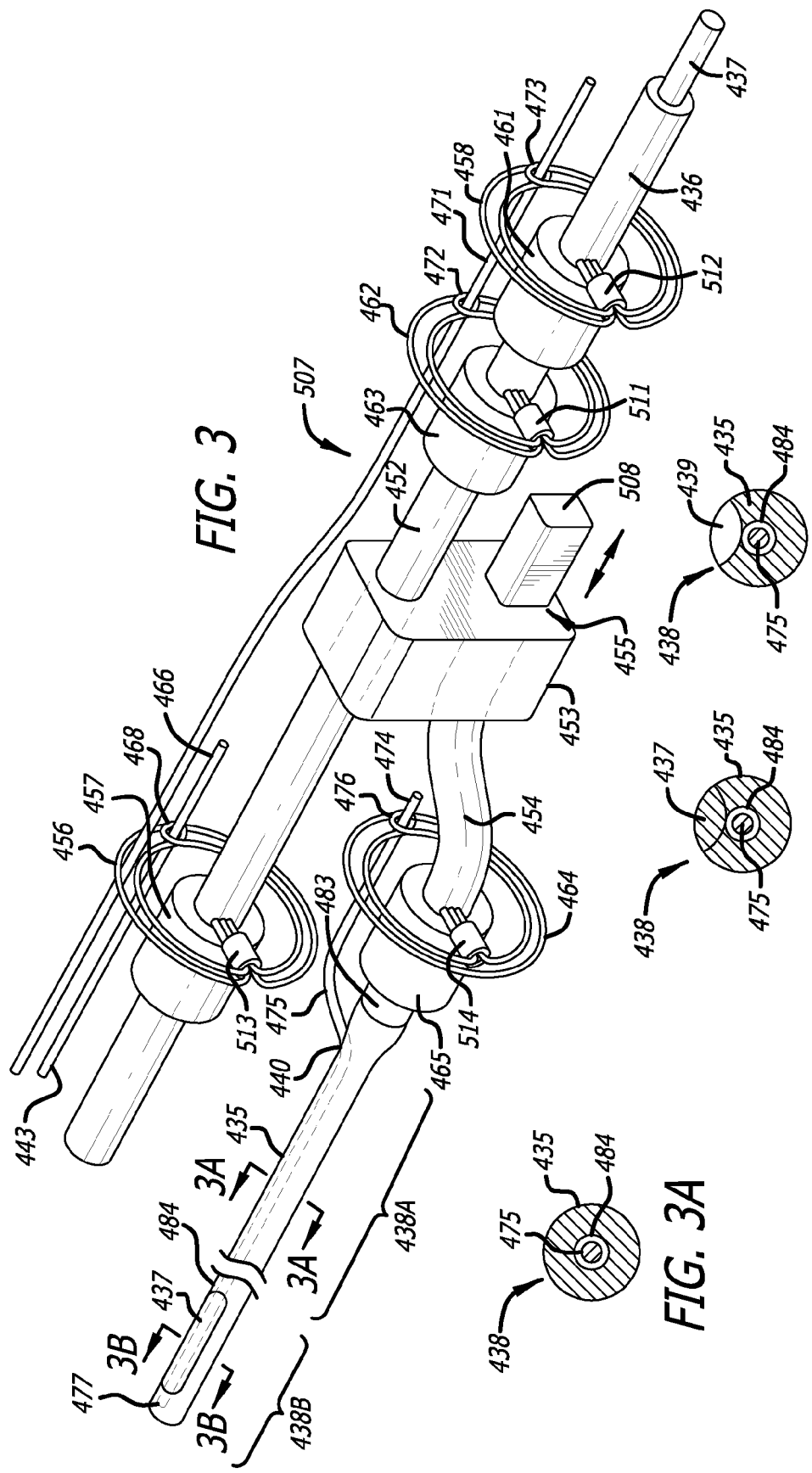
FIG. 3 is a perspective view of the belt support member assembly at a distal portion of the delivery system of FIG. 2.

FIGS. 2 and 3 illustrate a delivery system 400, for delivering an expandable intracorporeal device in the form of a bifurcated stent-graft 401, that is a first embodiment of the present invention. The illustrated graft 401 is shown as an example, but the present invention is not limited to use with such grafts and can be utilized with various grafts and other structures. Furthermore, while the illustrated stent-graft 401 is shown as a bifurcated graft, it may alternatively be a modular stent-graft with separate components which are attached to one another after insertion. In the illustrated embodiment, the graft 401 includes a main body portion 402 at a distal end 403 thereof that has a generally tubular cross-sectional profile when the graft takes on an expanded or deployed configuration. An ipsilateral leg 404 and a contralateral leg 405 (short leg), each having a substantially tubular configuration when expanded or deployed, branch from the main body portion 402 at bifurcation 406 and extend in a proximal direction from the bifurcation 406. The ipsilateral leg 404 terminates proximally with a proximal self-expanding member 407 and the contralateral leg 405 terminates proximally with a proximal self-expanding member 408.

A second distal self-expanding member 411 is disposed at a distal end 412 of the main body portion 402 of the graft 401 as with the graft embodiments previously discussed. Also, as with other endovascular graft embodiments discussed herein, the graft 401 may have inflatable channels and inflatable cuffs that serve, among other functions, to provide support for the graft 401 and the inflatable channels and cuffs can have configurations which are the same or similar to those inflatable channels and cuffs of other graft embodiments discussed herein, as well as other configurations. A distal inflatable cuff 413 is disposed at the distal end of the main body portion 402. Proximal inflatable cuffs 414 and 415 are disposed on the ipsilateral leg 404 and the contralateral leg 405, respectively. Inflatable channels 418 are fluid tight conduits which connect the inflatable cuffs 413, 414 and 415. The inflatable channels 418 and inflatable cuffs 413 and 414 are inflatable through an inflation port 421 that may be disposed at or near the proximal end of the ipsilateral leg 404. The inflation port 421 may alternatively be disposed at or near the proximal end 417 of the contralateral leg 405, or it may be disposed on other portions of the device as necessary. Generally, the structure and the materials used in the graft 401 (both the graft portion and the self-expanding members) can have various structures. In one particular embodiment, the main body portion and legs of the graft are made of expanded polytetrafluoroethylene (ePTFE) and the self-expanding members are made of nickel titanium, stainless steel or the like.

A first distal self-expanding member 422 is secured to the second distal self-expanding member 411 as shown in FIG. 2. The first and second distal self-expanding members 422 and 411 may be deployed in any desired sequence. In a particular embodiment having first and second distal self-expanding members, it may be desirable to first deploy the second distal self-expanding member 411 prior to deploying the first distal self-expanding member 422. Deploying the second distal self-expanding member 411 first may allow the operator to accurately adjust the axial position of the graft in the body lumen or vessel to within one to several millimeters before deploying the first distal self-expanding member 422. Using this technique, deployment of the second distal self-expanding member 411 alone provides sufficient resistance to axial displacement of the graft 401 for the graft position to be maintained in normal blood flow, but still allows deliberate axial displacement by the operator to achieve a desired axial position. This may be particularly important if tissue-penetrating members are included on the distal-most or first distal self-expanding member 422. If such tissue penetrating members are used on the first distal self-expanding member 422, axial movement may be difficult or even impossible once this member 422 is deployed without risking damage to the body lumen or vessel. As such, accurate axial placement of the graft 401 prior to deployment of the first distal self-expanding member 422 can be critical.

In addition, although not shown in the figures, this graft embodiment 401 may include two or more proximal self-expanding members disposed on one or both of the ipsilateral leg 404 and/or contralateral leg 405. These self-expanding members may have a configuration similar to that of the first and second distal self-expanding members 411 and 422

FIG. 2 shows delivery system 400 in partial section having an elongate shaft 423 with a proximal end 424, a distal end 425 and a distal section 426. A proximal adapter 427 is disposed at the proximal end 424 of the elongate shaft 423 and houses the controls that enable the operator to manipulate elements at the distal section 426 of delivery system 400 to release and deploy the graft 401, including inflating the graft channels 418 and cuffs 413, 414 and 415. The elongate shaft 423 has an inner tubular member 430 and an outer tubular member 431 disposed about the inner tubular member 430. The outer tubular member 431 is generally configured to slide in an axial direction over the inner tubular member 430. A proximal end 432 of the inner tubular member 430 is secured to or disposed on the proximal adapter 427. The inner and outer tubular members 430 and 431 may be made of polymeric materials, e.g., polyimides, polyester elastomers (HYTREL™), or polyether block amides (PEBAX™), and other thermoplastics and polymers. The proximal adapter 427 is generally fabricated from a polymeric material such as polyethylene, acetal resins (DELRIN™), etc., but can also be made from any other suitable material.

Bifurcated stent graft 401 is shown in FIG. 2 disposed within the distal section 426 of the elongate shaft 423 in a constrained configuration. The outer tubular member 431 is disposed about the graft 401 in the constrained state but can be retracted proximally so as to expose the constrained graft 401 by proximally retracting a proximal end 433 of the outer tubular member 431.

FIG. 2 shows the inner tubular member 430 disposed within the outer tubular member 431 and the guidewire tube 436 disposed within the inner tubular member 430. The guidewire tube 436 may be made from polymeric materials such as polyimide, polyethylene, polyetheretherketones (PEEK™).

A release member tube in the form of a release wire tube 441 is disposed about a distal primary release member in the form of a distal primary release wire 442. The release wire tube 441 is also disposed about a proximal primary release member in the form of a proximal primary release wire 443. Both the release member tube 441 and an inflation tube 444 are disposed within an inner lumen 445 of the inner tubular member 430.

A potted portion 446 is disposed between an inner surface of a distal end of the inner tubular member 430, the release wire tube 441, the guidewire tube 436 and the inflation tube 444. The potted portion 446 seals the inner lumen 445 of the inner tubular member 430 from bodily fluids that are exposed to the constrained graft 401 and potted portion 446 once the outer tubular member 431 is proximally retracted. The potted portion 446 may be made from adhesives, thermoforming plastics, epoxy, metals, or any other suitable potting material. Alternatively, a molded or machined plug may be bonded or affixed to the distal end of the inner tubular member, with lumens to accommodate the passage of tubes 441, 436 and 444.

A distal section 451 of the guidewire tube 436 serves as a primary belt support member 452 and is disposed within the main body portion 402 and ipsilateral leg 404 of the graft 401. Alternatively, the primary belt support member 452 may be disposed adjacent the graft main body portion 402 and ipsilateral leg 404. A secondary belt support member housing 453 is secured to the primary belt support member 452. An additional length of guidewire tube or other elongate member serving as a secondary belt support member 454 is slidably disposed within an appropriately configured lumen 455 of the housing 453. The secondary belt support member 454 is shown disposed within the graft main body portion 402 and contralateral leg 405; however, the secondary belt support member 454 may also be disposed adjacent the contralateral leg 405, regardless of whether the primary belt support member 452 is disposed adjacent or within the main body portion 402 and ipsilateral leg 404.

The secondary belt support member housing lumen 455 and secondary support member 454 cross sections may be keyed, singly or in combination, to allow relative sliding motion without relative rotation motion and therefore limit any twisting of the secondary support member 454 and the contralateral leg 405. The secondary belt support member 454 may be made from alloys such as nickel titanium, stainless steel, or polymeric materials such as polyimide.

A proximal primary belt 456 is shown disposed about and radially constraining the proximal self-expanding member 407 of the ipsilateral leg 404. This proximal self-expanding member 407 in turn is disposed about a bushing 457 that is shown as cylindrical in form, but which may have other configurations as well. The bushing 457 is secured to the primary belt support member 452 adjacent the proximal self-expanding member 407 of the ipsilateral leg 404.

A first distal primary belt 458 is disposed about and radially constraining the first distal self-expanding member 422, which itself is disposed about a cylindrical bushing 461. A second distal primary belt 462 is disposed about and radially constraining the second distal self-expanding member 411 and the second distal self-expanding member 411 is disposed about a cylindrical bushing 463.

A secondary belt 464 is shown disposed about and radially constraining the proximal self-expanding member 408 of the contralateral leg 405. This proximal self-expanding member 408 is disposed about a bushing 465 that is cylindrical in shape.

The belts 456, 458, 462 and 464 are typically made from nickel titanium, an alloy that is capable of exhibiting a unique combination of high strain without elastic deformation, high strength and biocompatability. However, any other suitable materials may be used including other metallic alloys such as stainless steel, high strength fibers such as carbon, KEVLAR™, polytetrafluoroethylene (PTFE), polyimide, or the like.

A distal portion 466 of the proximal primary release wire 443 is disposed within end loops 468 of the proximal primary belt 456 so as to releasably secure the proximal self-expanding member 407 of the ipsilateral leg 404 in a constrained state. The proximal primary belt 456 may be disposed about the self-expanding member 407 in a hoop-like configuration. The proximal self-expanding member 407 exerts outward radial pressure on the releasably secured belt 456. The primary proximal release wire 443 is axially moveable within the end loops 468 of the proximal primary belt 456 to allow for release of the belt by proximal retraction of the primary proximal release wire 443 in the same manner as described above with respect to other embodiments of the present invention.

Likewise, a distal portion 471 of the distal primary release wire 442 is disposed within end loops 472 of the second distal primary belt 462 that radially constrains the second distal self-expanding member 411. The second distal primary belt 462 is formed in a hoop configuration about the second distal self-expanding member 411 and the second distal self-expanding member 411 exerts outward radial force on the second distal primary belt 462. The distal primary release wire 442 is axially moveable within the end loops 472 of the second distal primary belt 462 to allow for release of the radial constraint as discussed above with respect to the proximal primary release wire 443. The distal portion 471 of the distal primary release wire 442 is also disposed within end loops 473 of the first distal primary belt 458 and radially constrains the first distal self-expanding member 422 in a similar fashion.

Although the distal primary release wire 442 and proximal primary release wire 443 are shown as two separate components, the release wires 442 and 443 could be combined into a single release member, such as a branched release wire. A branched release wire is capable of releasing multiple belts in a desired sequence by proper configuration of the lengths of the various branches of the wire. The relative amount of the release wire extending beyond the looped ends of the belt controls the timing of the release of the belts. Alternatively, a single release wire may engage both distal and proximal primary belts 456, 458 and 462. As this single release wire 150 is moved proximally, the first distal primary belt 458 is first released, followed by the release of the second distal primary belt 462 and then release of the proximal primary belt 456.

A distal portion 474 of a secondary release member in the form of a secondary release wire 475 is disposed within end loops 476 of a secondary belt 464 that radially constrains the proximal self-expanding member 408 of the contralateral leg 405. The proximal self-expanding member 408 of the contralateral leg 405 exerts outward radial force on the secondary belt 464 when the self-expanding member 408 is in a constrained configuration. The secondary release wire 475 is axially moveable within the end loops 476 of the secondary belt 464.

A proximal end 477 of the secondary release wire 475 passes into an inner lumen 484 of a release strand tube 438, as seen in FIG. 3. The release strand tube 438 will be described in more detail hereinafter. The release wires 442, 443 and 475 are generally made from a biocompatible high strength alloy such as stainless steel, but can also be made from any other suitable materials. Examples include other metallic alloys such as nickel titanium, non-metallic fibers such as carbon, polymeric materials, composites thereof, and the like. The diameter and stiffness of the release wires 442, 443 and 475 can be selected in accordance with the diameter and stiffness of the belts 456, 458, 462 and 464. The configuration of the end loops 468, 472, 473 and 476 of the belts 456, 458, 462 and 464 may vary to suit the particular embodiment of the delivery system 400 and device to be delivered, as illustrated in FIGS. 7C-7H of U.S. Patent Application Publication No. US 2004/0138734, which is incorporated herein in its entirety by reference.

Referring to FIGS. 3 and 3A-3C, the release strand tube 438 of the present embodiment generally comprises a tubular body 435 extending between a distal end 438A and a proximal end 438B. The tubular body 435 is preferably manufactured from a thermoplastic material, for example, Pebax™ or nylon, with or without a radiopaque material, for example, tungsten, bismuth or barium sulfate, mixed therewith. The tubular body 435 defines a lumen 484 extending substantially the length thereof. In the present embodiment, the body 435 includes a single lumen 484, but as described in other embodiments, the tubular body 435 may define more than one lumen 484.

The lumen 484 of the present embodiment is configured to receive the secondary release wire 475 such that the proximal end 477 thereof is adjacent to the proximal end 438B of the release strand tube 438. The release strand tube 438 may configured with sufficient column strength to facilitate pulling of the release wire 475 relative thereto. Alternatively, a separate instrument or the like may be utilized. The present embodiment includes a through passage 440 extending from the outer surface of the tubular body 435 to the lumen 484. The secondary release wire 475 extends through the passage 440 and through the lumen 484. An access opening 439 is provided in the proximal end 438B of the release strand tube 438 to facilitate access to the proximal end 477 of the secondary release wire 475. During delivery of the device 400, while the proximal end 438B of the release strand tube 438 is being passed through the patient, a cover 437 is positioned over the access opening 439. The cover 437 may be retained by an adhesive or the like. When access to the secondary release wire 475 is desired, the cover 437 is peeled away to reveal the access opening 439 which is in communication with the lumen 484. Alternatively, the cover 437 may be an integral part of the tubular body 435 which is cut away when access to the secondary release wire 475 is desired. To prevent accidental deployment of the proximal self-expanding member 408, the cover 437 is preferably removed just prior to deployment, although such is not required.

Again referring to FIG. 3, the distal end 438A of the release strand tube 438 is connected directly to the proximal end 483 of the secondary belt support member 454. The release strand tube 438 may interconnected in various manners, including, but not limited to, adhesives, bonding, ultrasonic welding, metallic welding, hot melt bonding, compression fitting, barbs, or any other suitable means. Alternatively, the release strand tube 438 and the secondary belt support member 454 may be formed integral with one another, either from similar material or different materials, for example, using a multi-step molding process.

Referring to FIGS. 4-15, various configurations for the distal and proximal ends 438A and 438B of the release strand tube 438 will be described. In each of these embodiments, the tubular body 435' includes a first lumen 484 configured to receive the secondary release wire 475 and a second lumen 481 configured to receive a secondary support strand 481. The secondary support strand 481 is connected to the proximal end 483 of the secondary belt support member 454. As will be described hereinafter, in each embodiment, the secondary support strand 481 is in turn connected to the release strand tube 438. Movement of the release strand tube 438 will be translated through the secondary support strand 481 and result in a corresponding force on the secondary belt support member 454.

Figure 4:
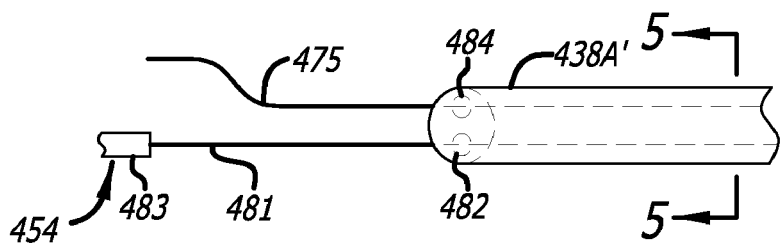
FIGS. 4 and 6-8 are perspective views of alternate embodiments of the distal end of the release strand tube of the present invention.
Figure 5:
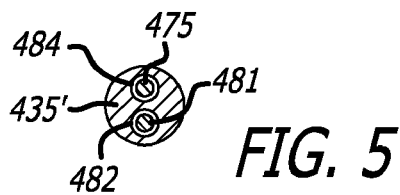
FIG. 5 is a cross-sectional view along the line 5-5 in FIG. 4.
Figure 6:
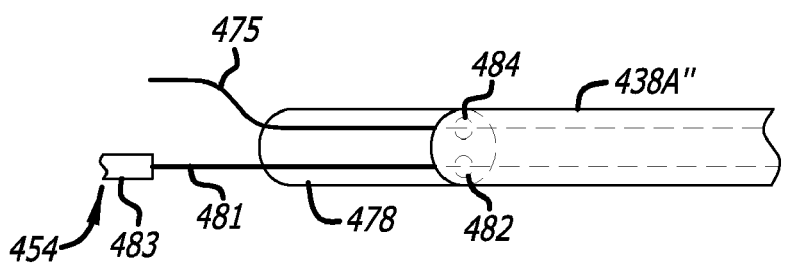
Figure 7:
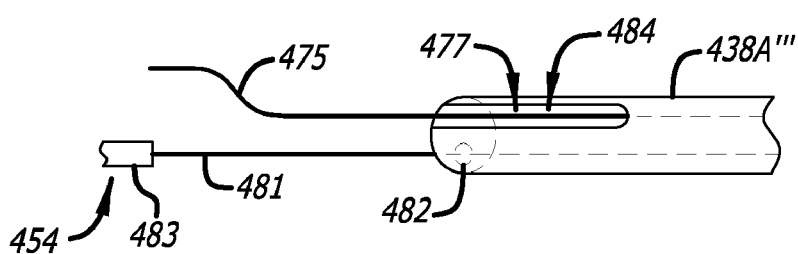
Figure 8:
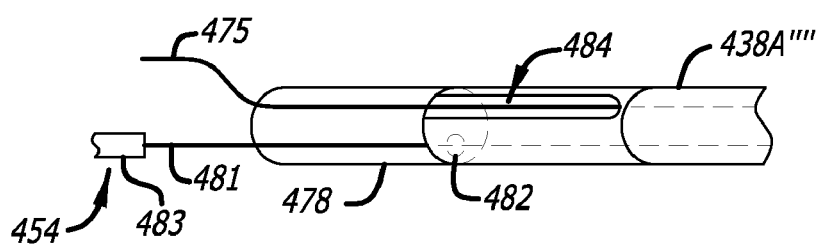

In the embodiment illustrated in FIG. 4, both of the lumens 482 and 484 extend to the distal face of the distal end 438A' of the release strand tube 438 and the corresponding strand/wire enters straight in to the respective lumen 482, 484. The embodiment of FIG. 6 is similar and again both of the lumens 482 and 484 extend to the distal face of the distal end 438A" of the release strand tube 438 and the corresponding strand/wire enters straight in to the respective lumen 482, 484. The distal portion 438A" further includes a tube 478 manufactured from tetrafluoroethylene or the like which surrounds the secondary support strand 481 and secondary release wire 475 to provide greater protection therefore. The tube 478 may be bonded, welded, heat shrunk or otherwise attached to the distal end 438A". Turning to FIG. 7, the lumen 482 extends to the front face of distal end 438''' and the secondary support strand 481 is received therein. To further facilitate entry of the secondary release wire 475 in to lumen 484, a portion of the upper surface of distal end 438A''' is removed at 477 to enlarge the opening into the lumen 484. The distal end 438A''' of FIG. 8 is similar to that of FIG. 7 and additionally includes the tube 478 as described with respect to FIG. 6.

Figure 9:
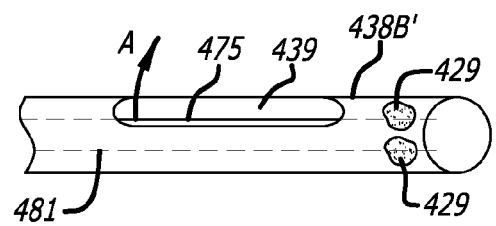
FIGS. 9-13 are perspective views of alternate embodiments of the proximal end of the release strand tube of the present invention.

Referring to FIGS. 9-14, various embodiments of the proximal end 438B of the release strand tube 438 will be described. The proximal end 438B' illustrated in FIG. 9 is similar to the embodiment of FIG. 3 and includes an access opening 439 to access the secondary release wire 475. In the present embodiment, the secondary release wire 475 is glued, bonded or otherwise adhered at 429 within the lumen 484 adjacent to the proximal end 438B'. As such, the secondary release wire 475 can be pulled up from the access opening 439 as indicated by arrow A, but will not come free from the lumen 484. Similarly, the secondary support strand 481 is glued, bonded or otherwise adhered at 429 within the lumen 482 adjacent to the proximal end 438B'. While secondary support strand 481 is illustrated as being bonded adjacent proximal end 438B', such is not required, and secondary support strand 481 may be bonded further distal along the lumen 482. Additionally, the secondary support strand 481 may be bonded at more than one location. As explained above, bonding of the secondary support strand 481 to the release strand tube 438 causes the secondary support strand 481, and thereby the secondary belt support member 454, to move with the release strand tube 438.

Figure 10:
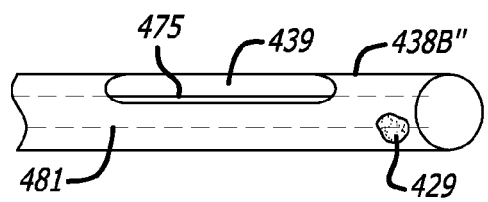

The proximal end 438B" of FIG. 10 is similar to the embodiment of FIG. 9, except that the secondary release wire 475 is not bonded, but instead is free to be pulled free through the access opening 439. In both embodiments of FIGS. 9 and 10, instead of a complete opening 439, such may be formed as a closed skive cut which is bent or the like to cause opening thereof as desired.

Figure 11:
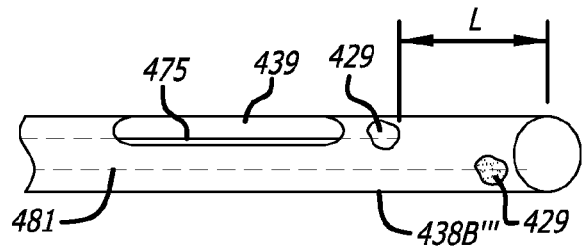

With respect to the proximal end 438B''' of the release strand tube 438 illustrated in FIG. 11, the secondary release wire 475 does not extend to the end of the tube, but instead terminates a distance L from the end. The secondary release wire 475 will still be accessible through the access opening 439 and may either be bonded, as illustrated, or free. The additional length L of the release strand tube 438 will be less rigid without the secondary release wire 475, which increases the ability to snag the release strand tube 438 during the initial passage thereof through the patient. Alternatively, the secondary support strand 481 may terminate a distance from the end, for example, prior to the access opening 439, while the secondary release wire 475 extends substantially to the end. In yet another embodiment, both the secondary release wire 475 and the secondary support strand 481 may terminate at least a distance L from the end of the release strand tube 438, thereby providing a substantially flexible proximal end 438B'''.

Figure 12:
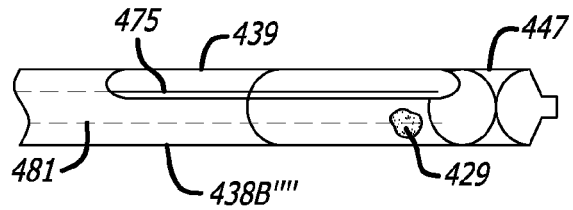

Referring to FIG. 12, the access opening 439 extends to the end of proximal end 438B'''', making the secondary release wire 475 easily accessible. To prevent entanglement or the like of the release wire 475 during passage of the release strand tube 438 through the patient, a heat shrink wrap 447 or the like may be provided over the proximal end 438B''''. The heat shrink wrap 447 may be made from tetrafluoroethylene, polyolefin or other suitable materials. The heat shrink wrap 447 may be configured to be removed prior to actuation of the secondary release wire 475 or the release wire 475 may be accessible through the access opening 439 with the heat shrink wrap 447 still on the proximal end 438B''''.

Figure 13:
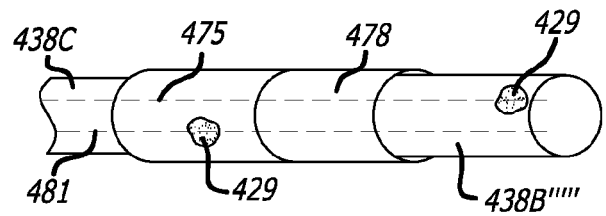
Figure 14:
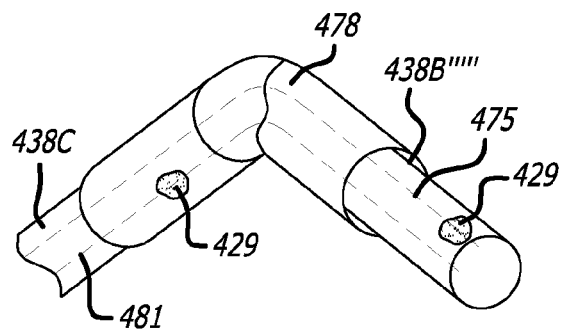
FIG. 14 is a perspective view of the proximal end of the release strand tube of FIG. 13 illustrating the end being separated to facilitate pulling of the secondary release wire.

Referring to FIGS. 13 and 14, a release strand tube 438 with a separable proximal end 438B''''' is illustrated. The proximal end 438B''''' abuts an intermediate portion 438C of the release strand tube 438 and is maintained thereto via a heat shrink tube 478. Other connecting means, for example, adhesives, welding, bonding, clips, straps or any other suitable means, may be used to interconnect the proximal end 438B''''' to the intermediate portion 438C. The intermediate portion 438C may be integral with or a separate component from the distal end 438A. The secondary release wire 475 extends into the proximal end 438B''''' and is bonded thereto as indicated at 429. The secondary support strand 481 may extend into the proximal end 438B''''', but is not bonded thereto. The secondary support strand 481 is bonded in the intermediate portion 438C or the distal end 438A. To actuate the secondary release wire 475, the proximal end 438B''''' is disconnected from the intermediate portion 438C, as illustrated in FIG. 14, by bending, twisting or the like to break the tube 478 in the illustrated embodiment. Other detachment mechanisms may be used if different connecting means are utilized. The proximal end 438B''''' can then be moved proximally relative to the intermediate portion 438C, thereby pulling the secondary release wire 475.

While FIGS. 3-14 illustrate various configurations of the release strand tube 438, other configurations may also be utilized without departing from the invention.

Referring again to FIG. 2, inflation port 421 extends proximally from the proximal end 416 of the ipsilateral leg 404 of the graft 401. The inflation port 421 is coupled to a distal end 487 of the inflation tube 444 by a retention mechanism, such as a retention wire 488. Typically, the retention wire 488 extends from the inflation port 421 proximally to the proximal adapter 427 of delivery system 400. The distal end 487 of the inflation tube 444 can be disengaged from the inflation port 421 by pulling on a proximal end 491 of retention wire 488. The retention wire 488 may be a small diameter wire made from a material such as a polymer, stainless steel, nickel titanium, other alloy or metal, or composite; in a particular embodiment of the invention, retention wire 488 may be a spring formed of a variety of suitable spring materials. Alternatively, the retention wire 488 may have a braided or stranded configuration.

FIG. 2 illustrates proximal adapter 427 which is suitable for use with embodiments of the present invention. The proximal adapter 427 houses the proximal termination of the primary release wires 442 and 443, guidewire tube 436, retention wire 488 and release wire tube 441. The proximal adapter 427 has a first side arm 492 with an inner lumen 493 that secures the proximal end of the release wire tube 441 and second side arm 499 having an inner lumen in fluid communication with inflation material lumen that houses proximal end 491 of retention wire 488. The proximal adapter 427 has a distal primary release wire handle 495 and a proximal s primary release wire handle 496 that are disposed in a nested configuration on the first side arm 492. A proximal end of the proximal primary release wire 443 is secured to the proximal primary release-wire handle 496. A proximal end of the distal primary release wire 442 is secured to the distal primary release wire handle 495. This configuration prevents the operator from inadvertently deploying or activating the proximal primary release wire 443 prior to deployment or activation of the distal primary release wire 442 which could result in an undesirable graft 401 deployment sequence. Various proximal adapters 427 are illustrated in U.S. Patent Application Publication No. US 2004/0138734, which is incorporated herein in its entirety by reference.

FIG. 3 illustrates a belt support member assembly 507 of the delivery system 400. The distal end 508 of the secondary belt support member 454 is slidingly disposed within the secondary belt support member housing 453 that is secured to the primary belt support member 452. The second distal primary belt 462 is secured to the primary belt support member 452 (which in this embodiment is the guidewire tube 436) and extends radially therefrom through an optional second distal primary standoff tube 511. Similar optional first distal primary standoff tube 512, proximal primary standoff tube 513 and optional secondary standoff tube 514 are disposed on the first distal primary belt 458, proximal primary belt 456 and secondary belt 464, respectively.

Figure 15:
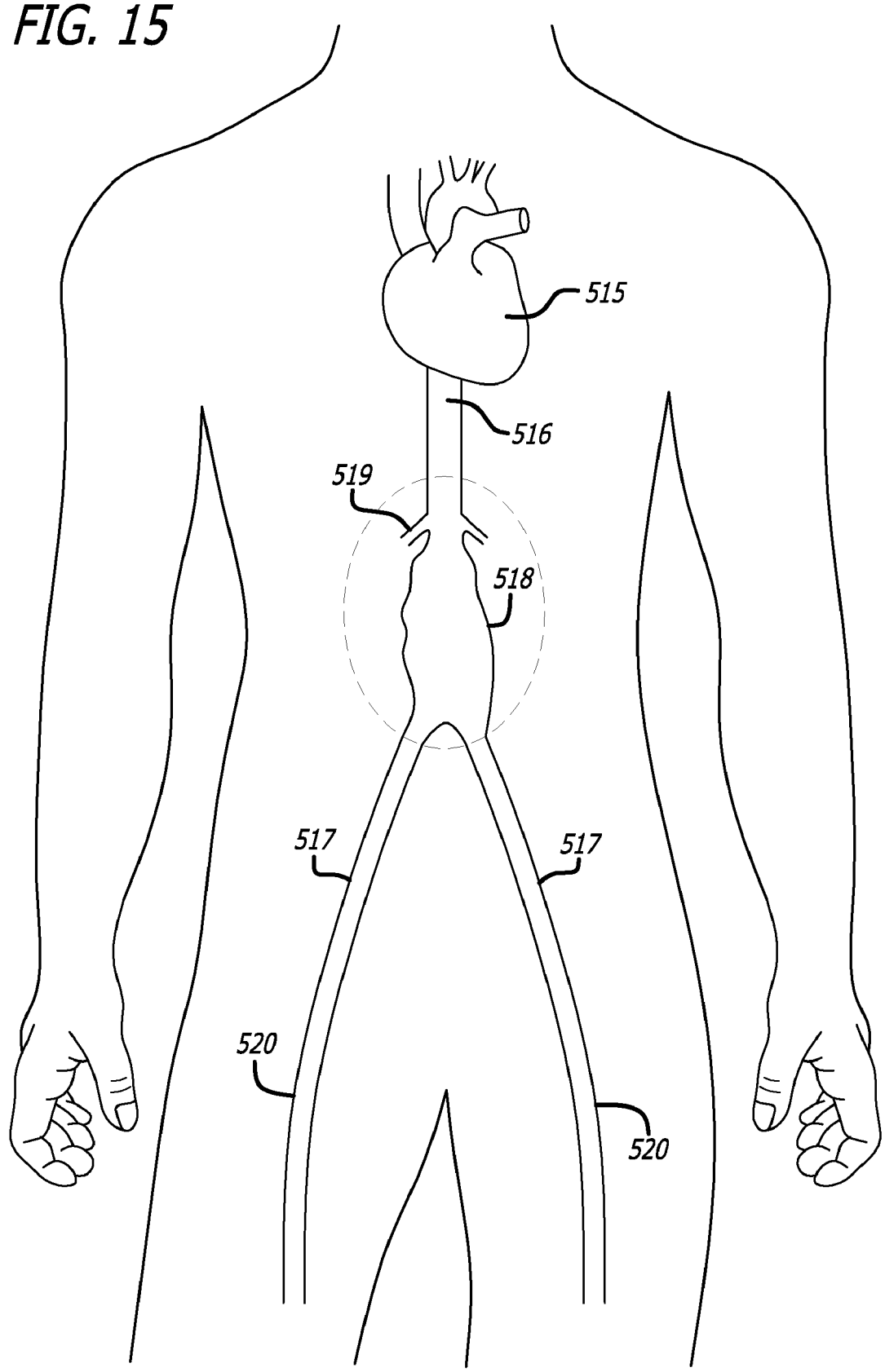
FIG. 15 illustrates a portion of the internal vasculature of a patient, including the aorta, iliac and femoral arteries branching therefrom.

Having described the components of the various embodiments of the delivery system 400, operation of an illustrative embodiment will be described with reference to FIGS. 15-32. FIG. 15 illustrates generally the anatomy of a patient's heart 515, aorta 516 and iliac arteries 517. The aorta 516 extends from the heart 515 and descends into the abdomen of the patient's body. An aneurysm 518 is disposed in the aorta 516 just below the renal arteries 519. The aorta 516 branches into the right and left iliac arteries 517 below the aneurysm, which then become the femoral arteries 520.

Figure 16:
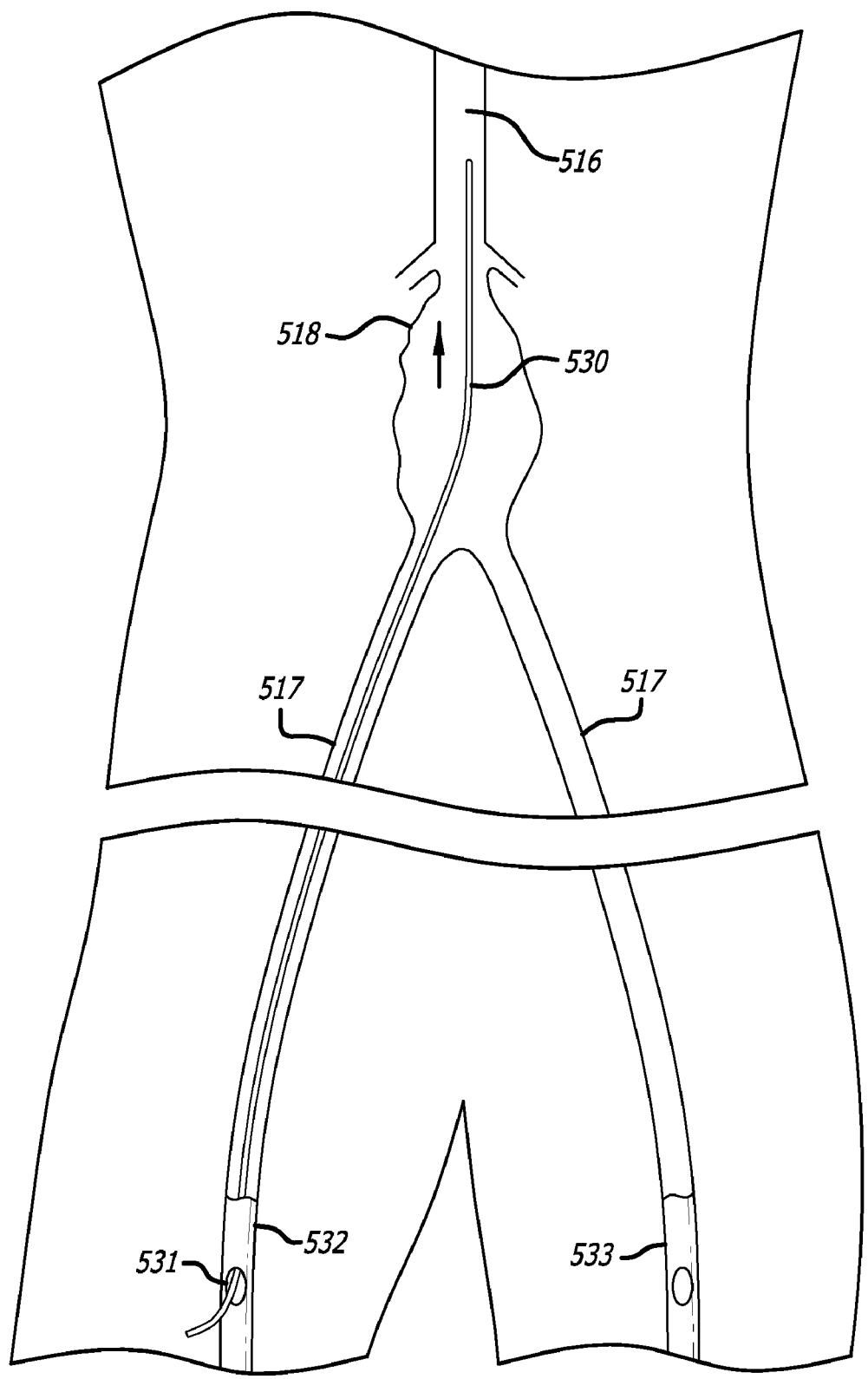
FIG. 16 is a magnified view of the abdominal aorta area of the patient shown in FIG. 15 and shows a guidewire positioned in the aorta from the right iliac artery.

One delivery procedure of the present invention begins with delivery of a first guidewire 530 into an access hole 531 in a femoral artery, the right femoral artery 532 for the procedure depicted in FIG. 16, and advanced distally through the iliac artery 517 and into the patient's aorta 516. Access into the femoral artery 532 is generally accomplished with a standard sheath and trocar kit, although sheathless access may also be employed. It should be noted that although the procedure described herein and illustrated in FIGS. 15-32 is initiated in the right femoral artery 532, the same procedure could be carried out beginning in the left femoral artery 533 with the orientation reversed.

Figure 17:
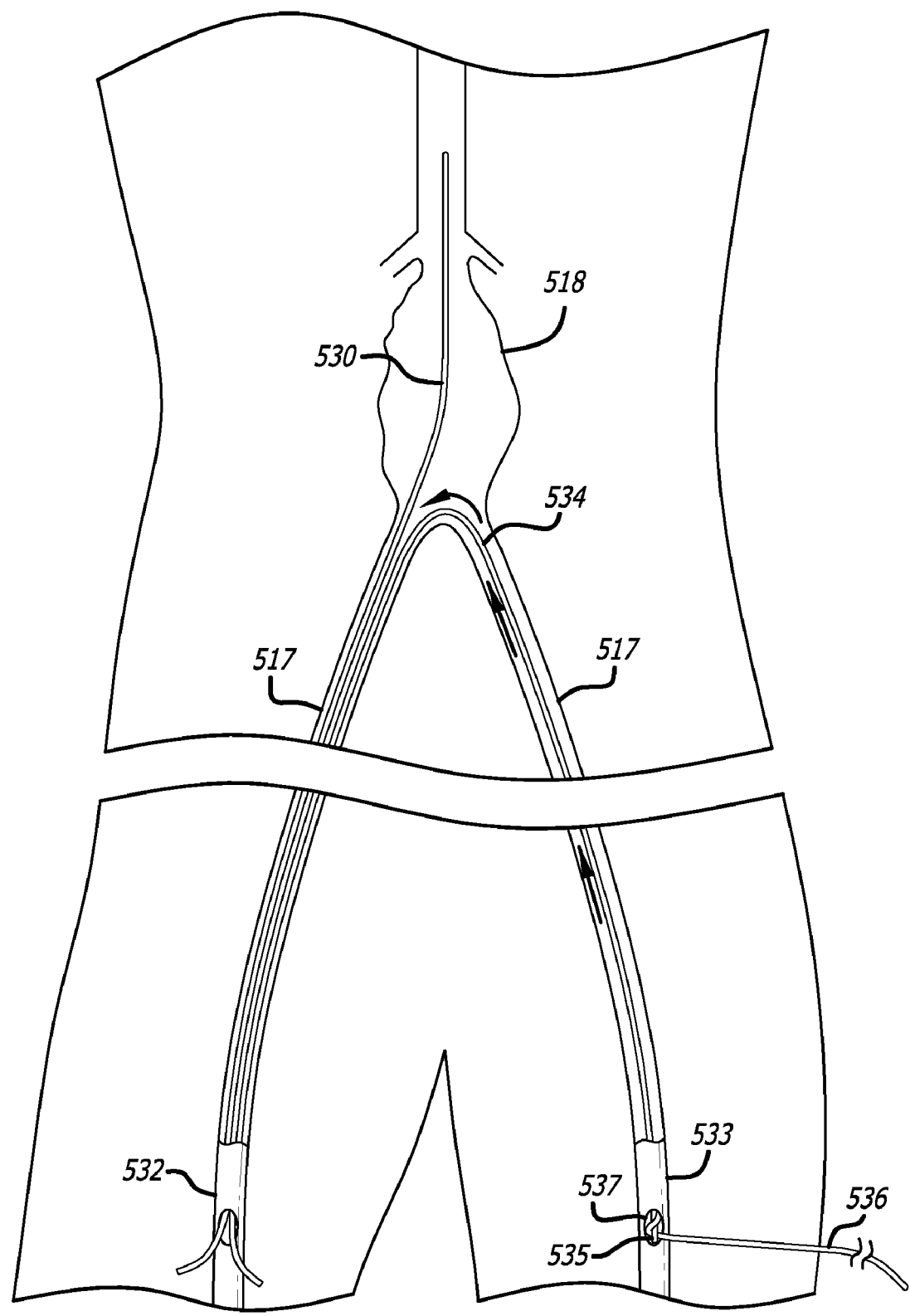

Referring to FIG. 17, with the first guidewire 530 positioned across the aneurysm 518, a second guidewire 534 is then introduced into the ipsilateral or right femoral artery 532 and guided into the iliacs 517 and then back down into the contralateral or left femoral artery 533. A distal end 535 of the second guidewire 534 may then be captured with a snare 536 or similar device inserted through an access hole 537 in the left femoral artery 533. The distal end 535 of the second guidewire 534 may then be pulled out of the left femoral artery 533 through the same left femoral artery access hole 537, providing a continuous length of wire passing through each iliac artery 517 via the left and right femoral artery access holes 537 and 531, as shown in FIG. 17.

Figure 18:
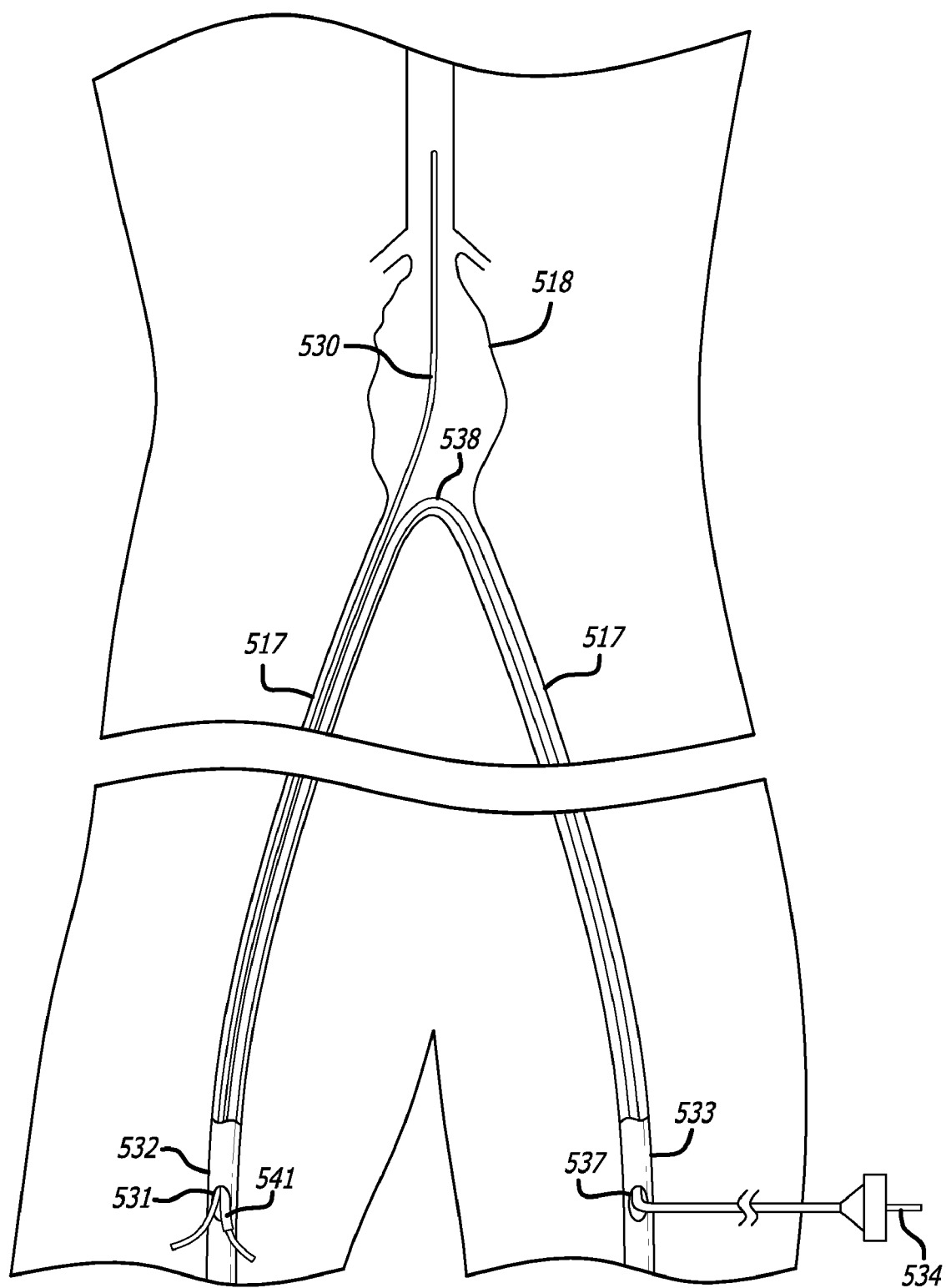
Figure 19:
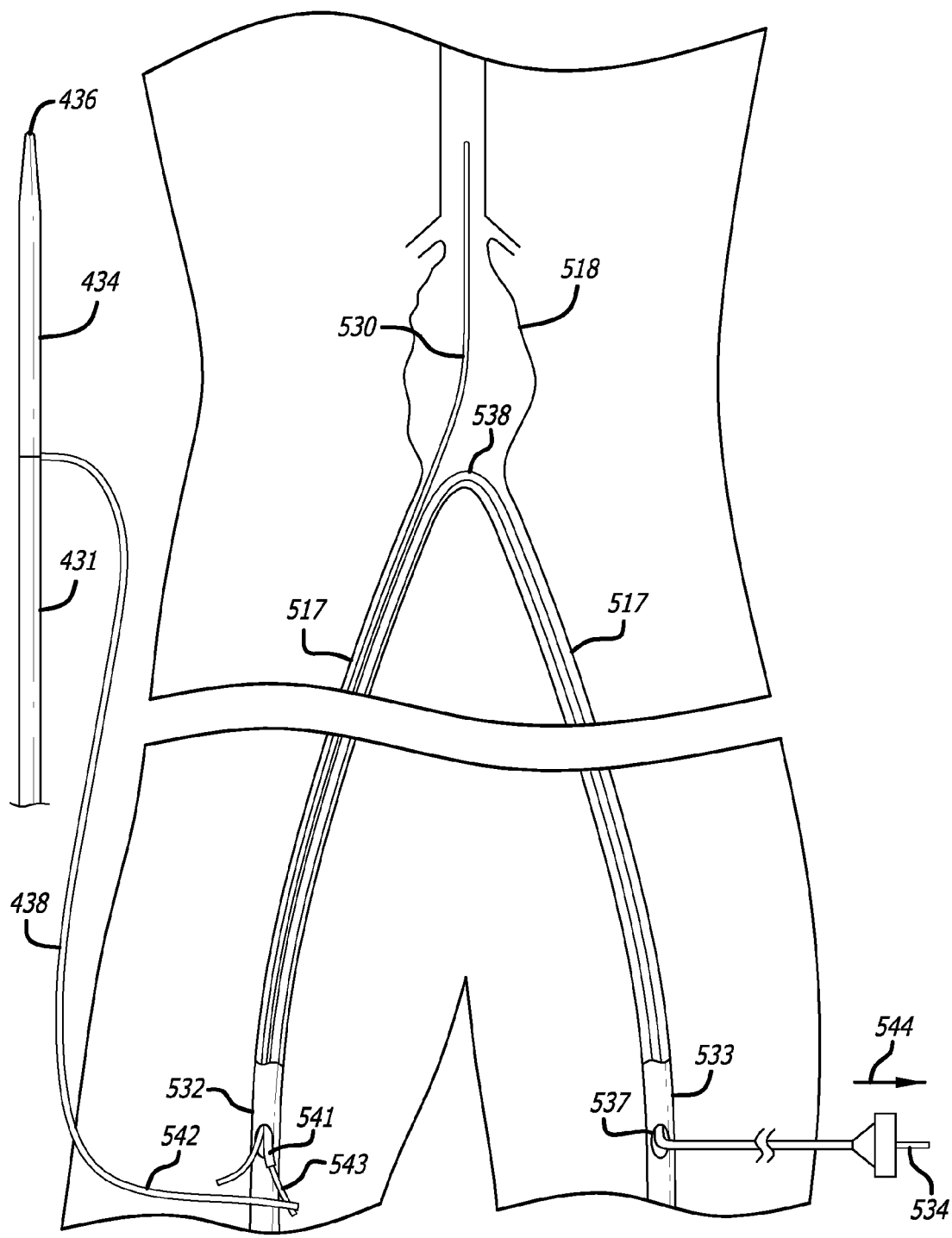

Once the second guidewire 534 exits the access hole 537 in the left femoral artery 533, a tubular catheter 538 may be advanced over the second guidewire 534 through the left femoral artery access hole 537 so as to extend out of the body from the access hole 531 in the right femoral artery 532 as shown in FIG. 18. This provides a continuous conduit between the right and left iliac arteries 517. With a distal end 541 of the tubular catheter 538 extending from the access hole 531 in the right femoral artery 532, a distal end 542 of the release strand tube 438 may then be affixed to a proximal end 543 of the second guidewire 534 as shown in FIG. 19. Each of the various embodiments of the release strand tube 438 described above may be utilized herein. Other variations of this tube are also within the scope of the present invention.

Figure 20:
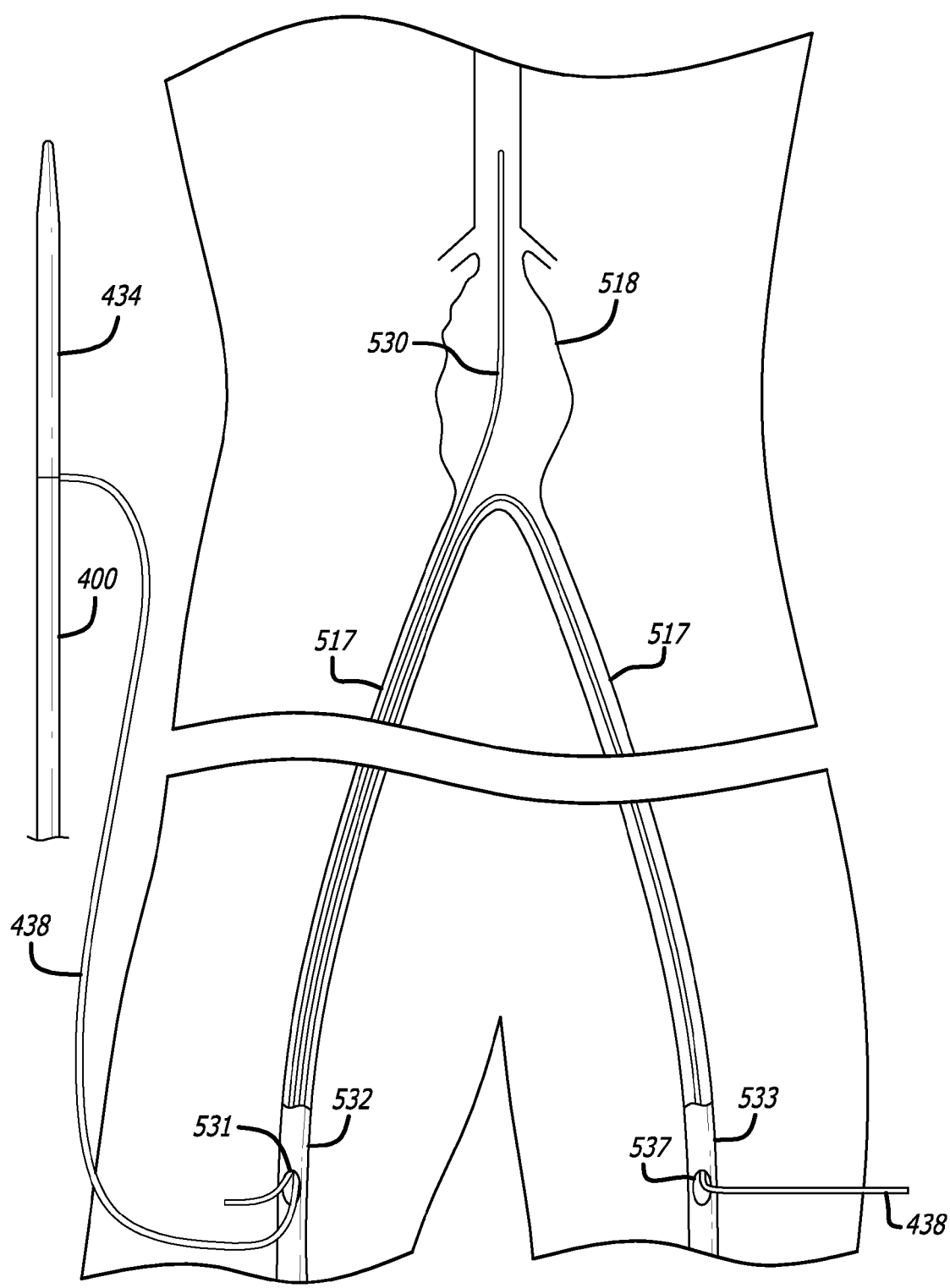

The second guidewire 534 is then pulled out of the tubular catheter 538 from the left femoral artery access hole 537, in the direction indicated by the arrow 544 in FIG. 19, so that the release strand tube 438 then extends through the tubular catheter 538 from the right iliac artery to the left iliac artery. The tubular catheter 538 may then be withdrawn, leaving the release strand tube 438 extending through the left and right iliac arteries 517 from the access hole 531 in the right femoral artery 532 to the access hole 537 in the left femoral artery 533, as shown in FIG. 20. The first guidewire 530 remains in position across the aneurysm 518.

Figure 21:
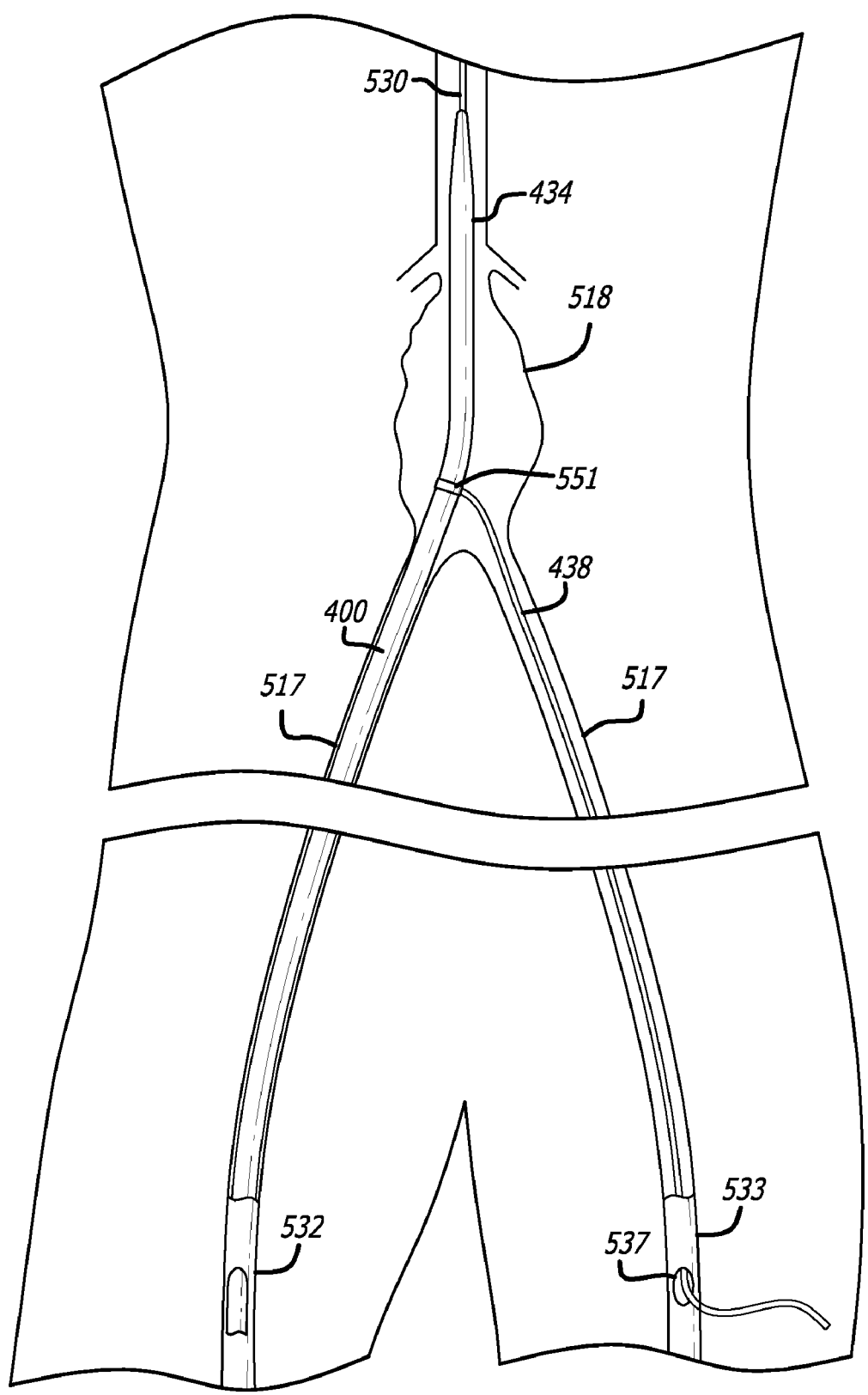

Referring to FIG. 21, the delivery system 400 is then advanced into the patient's right femoral artery 532 through the access hole 531 over the first guidewire 530. It may be desirable to apply tension to the release strand tube 438 as the delivery system 400 is advanced to the vicinity of the aneurysm 518 so as to remove slack in the tube 438 and prevent tangling thereof or the like. Tension on the release strand tube 438 may also help to prevent twisting of the delivery system 400 during insertion.

An optional marker band 551 may disposed adjacent nosepiece 434 or generally in the vicinity of the distal end of the delivery system 400. Such a marker band 551 may also be integral with the delivery system 400; for example, it may be incorporated as part of the distal nosepiece 434. A useful marker 551 can be one that does not add to the profile of the delivery system 400. Such a marker may be used to aid the operator in introducing the delivery system 400 without twisting. Various types of marker bands are described in U.S. Patent Application Publication No. US 2004/0138734, which is incorporated herein in its entirety by reference.

Figure 22:
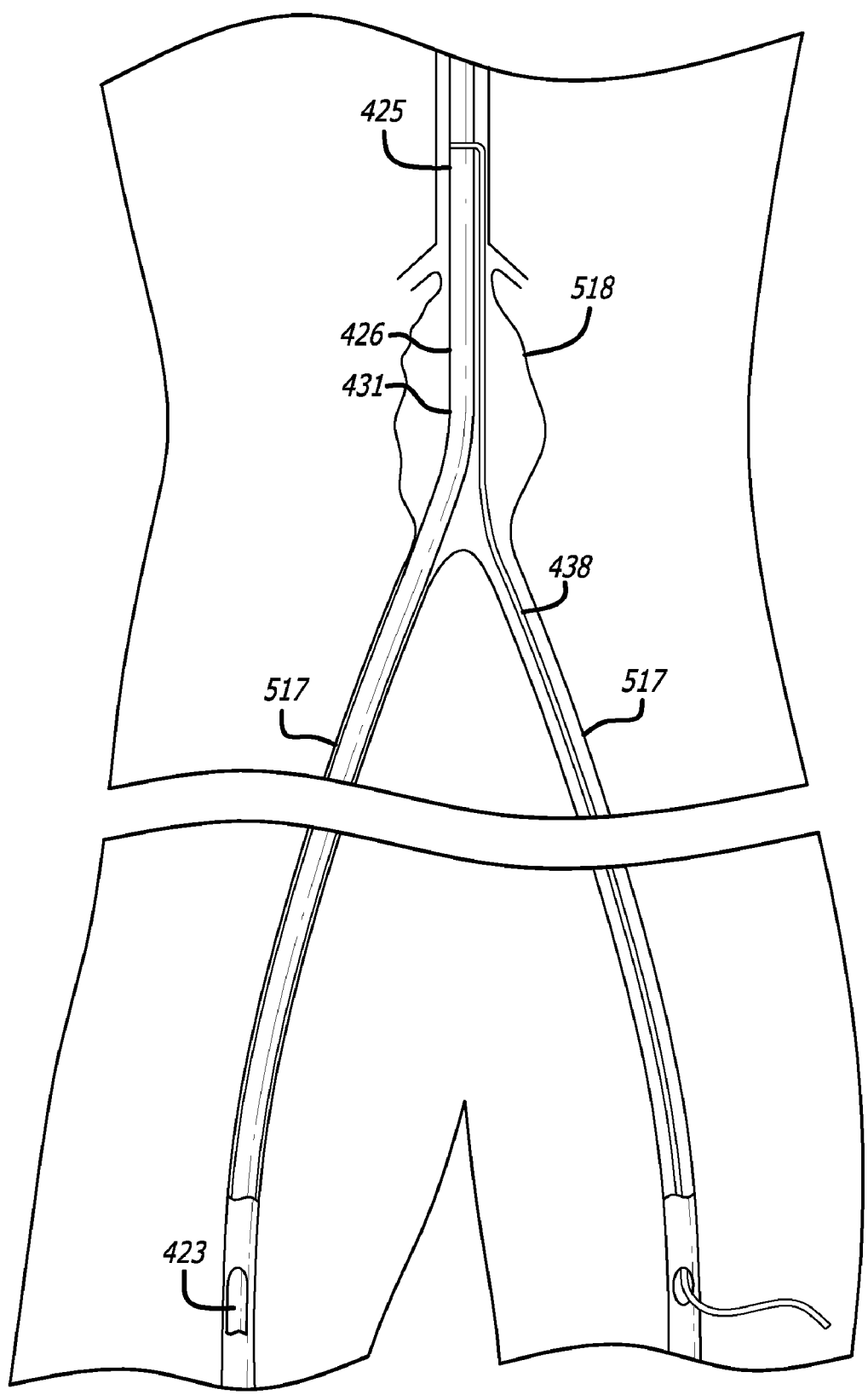

The delivery system 400 is positioned in a location suitable for initiating the deployment process, such as one in which the distal end 425 of the delivery system 400 is disposed beyond, or distal to the position in which the graft 401 will be placed, as shown in FIG. 22. This position allows the proximal end 483 of the secondary belt support member 454 to be laterally displaced without mechanical interference from the patient's vasculature.

Once the distal section 426 of the elongate shaft 423 and the endovascular graft 401 are positioned, the deployment process is initiated. First, the outer tubular member 431 is proximally retracted by pulling on the proximal end 433 of the outer tubular member 431 relative to the inner tubular member 430. The inner tubular member 430 should be maintained in a stable axial position, as the position of the inner tubular member 430 determines the position of the constrained bifurcated graft 401 prior to deployment. Upon retraction of the outer tubular member 431, the constrained bifurcated graft 401 is exposed and additional slack is created in the release strand tube 438 as shown in more detail in FIG. 23.

Alternatively, a variety of different components may be substituted for the outer tubular member 431 in some of the embodiments of the invention. For instance, a shroud, corset, mummy-wrap, or other cover may be released or actuated to expose the constrained graft 401 after the delivering system 400 is introduced into the vasculature.

Figure 23:
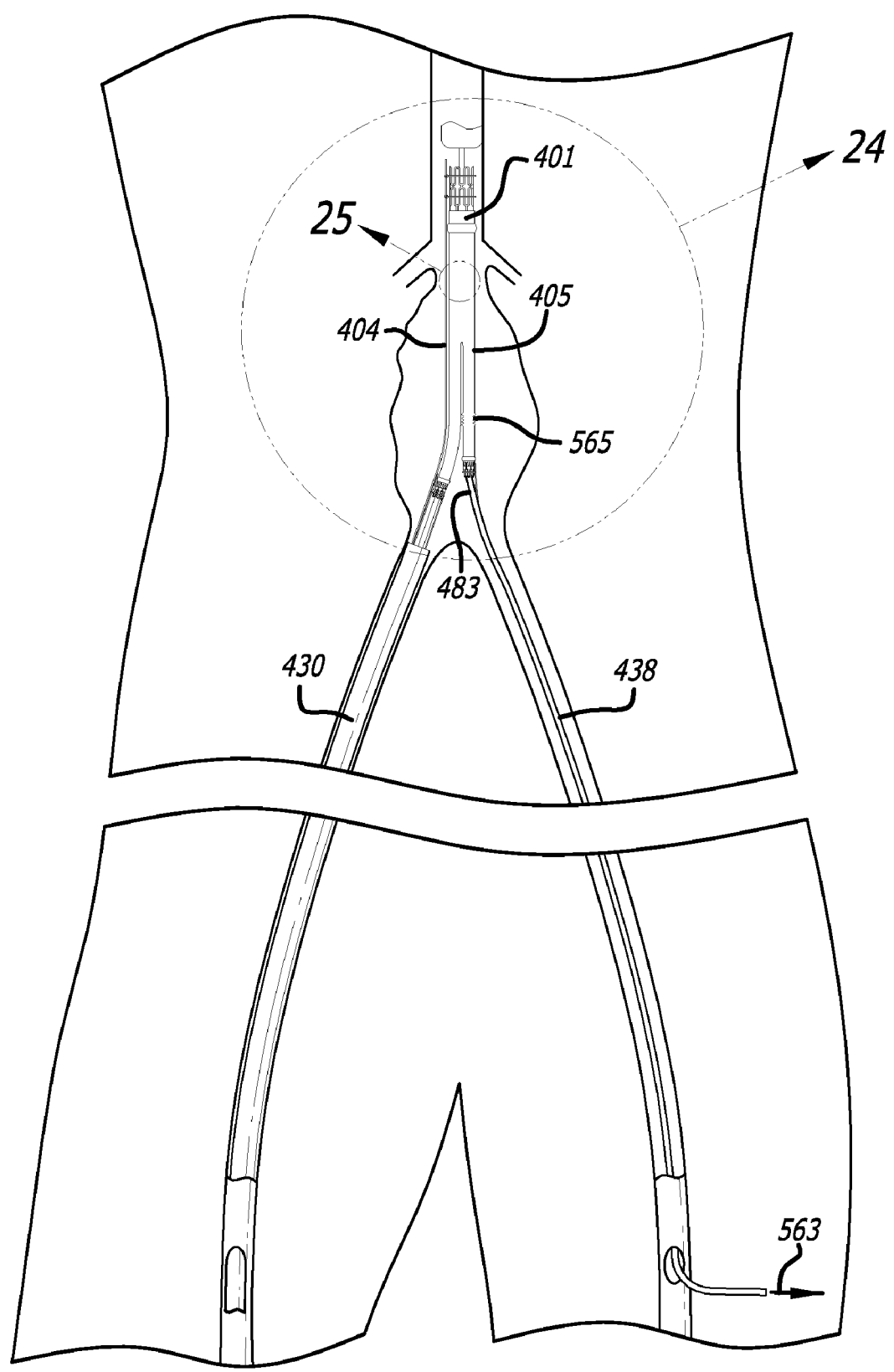

The slack in the release strand tube 438 is taken up by applying tension to the release strand tube 438 as shown by the arrow 563 in FIG. 23. Since, in the present embodiment, the release strand tube 438 is connected directly to the secondary belt support member 454, tension on the release strand tube 438 is applied directly to the secondary belt support member 454. As such, the secondary belt support member 454 begins to slide within the secondary belt support member housing 453 in a proximal direction as shown by the arrow 564 in FIG. 25. The secondary belt support member 454 continues to slide proximally until all the slack is removed from an axially compressed or folded portion 565 of the contralateral leg 405 of the graft 401 shown in FIG. 24 and the primary and secondary belt support members 452 and 454 are oriented relative to the secondary belt support member housing 453 as generally shown in FIG. 26. Rotational movement of the secondary belt support member 454 relative to the secondary belt support member housing 453 is prevented by the non-circular or asymmetric cross section of the member 454 as shown in FIG. 3. This prevents the contralateral leg 405 from twisting or becoming entangled with other components of the graft 401 or delivery system 400 during deployment.

Axial compression of all or a portion of the contralateral leg 405 while the graft 401 is in a constrained state within the delivery system 400 prior to deployment allows the axial position of the two proximal self-expanding members 407 and 408 to be axially offset from each other. Alternatively, graft legs 404 and 405 having different lengths may be used to prevent overlap of the self-expanding members 407 and 408 within the delivery system 400. The cross sectional profile or area of the overlap self-expanding members 407 and 408 is generally greater than that of the adjacent polymer material portion of the legs 404 and 405 of the graft 401, so eliminating the overlap can be desirable. The self-expanding members 407 and 408 are typically made of a metal or metallic alloy and maintain a cylindrical configuration, even when in a constrained state. The polymer material of the legs 404 and 405 or main body portion 402 of the graft 401, by contrast, is relatively soft and malleable and can conform to the shape of whatever lumen in which it may be constrained. Placing both proximal self-expanding members 407 and 408 adjacent each other in a compressed state at a single axial position within the delivery system 400 would require a configuration in which two objects having an approximately circular cross section are being placed within another circular lumen. Such a configuration generates a significant amount of wasted or unused cross sectional area within that axial position of the delivery system 400 and would likely result in less flexibility and greater cross section than a delivery system 400 in which the proximal self-expanding members 407 and 408 are axially offset.

Figure 27:
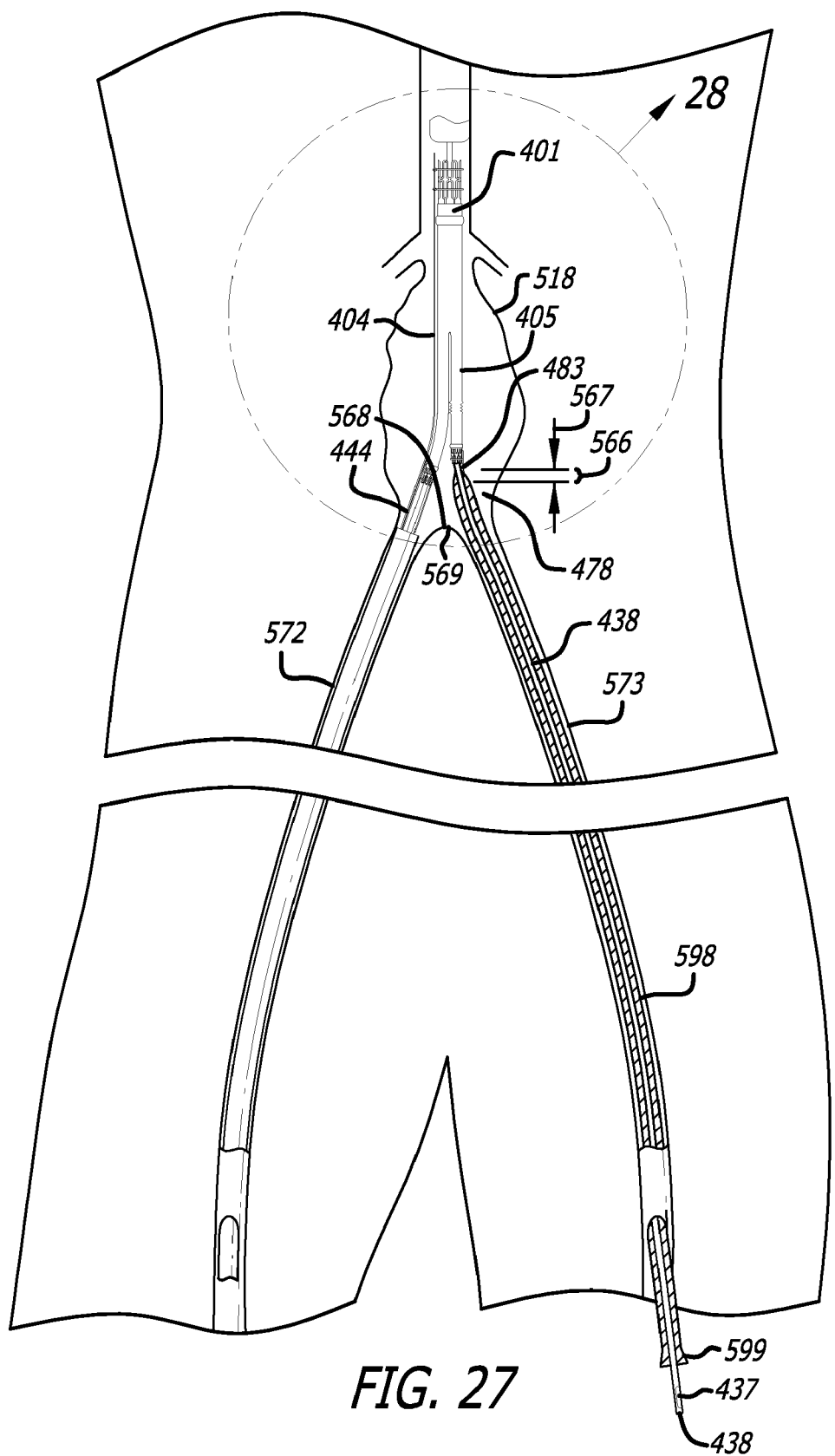

A gap 566 indicated by the arrows 567 in FIG. 27 allows the proximal end 483 of the secondary belt support member 454 to move in a lateral direction without mechanical interference from the carina 568 of the iliac artery bifurcation 569.

Gap 566 may vary depending on the patient's particular anatomy and the specific circumstances of the procedure.

The lateral movement of the contralateral leg 405 and secondary belt support member 454 is accomplished by application of tension on the release strand tube 438. This movement away from the primary belt support member 452 allows the secondary belt support member 454 to transition from alignment with the right iliac artery 572 to alignment with the left iliac artery 573 as shown in FIG. 27. As illustrated in FIGS. 27-31, an obturator 598 may be utilized to assist in moving and positioning the secondary belt support member 454 and the contralateral leg 405. The obturator 598 is slid over the release strand tube 438 and can be connected thereto with a hemostatic valve 599 or the like. The size of the release strand tube 438, relative to the small diameter strands, is large enough such that the hemostatic valve 599 provides a secure connection between the obturator 598 and the release strand tube 438. As such, movement of the obturator 598 will directly control movement of the release strand tube 438, and thereby the secondary belt support member 454 which is attached thereto. Even in the multi-lumen embodiments of the release strand tube 438 illustrated in FIGS. 4-14, the secondary support strand 481 is connected to the release strand tube 438 at one or more points, such that operation of the obturator 598 will allow for easy control of the secondary belt support member 454.

Figure 28:
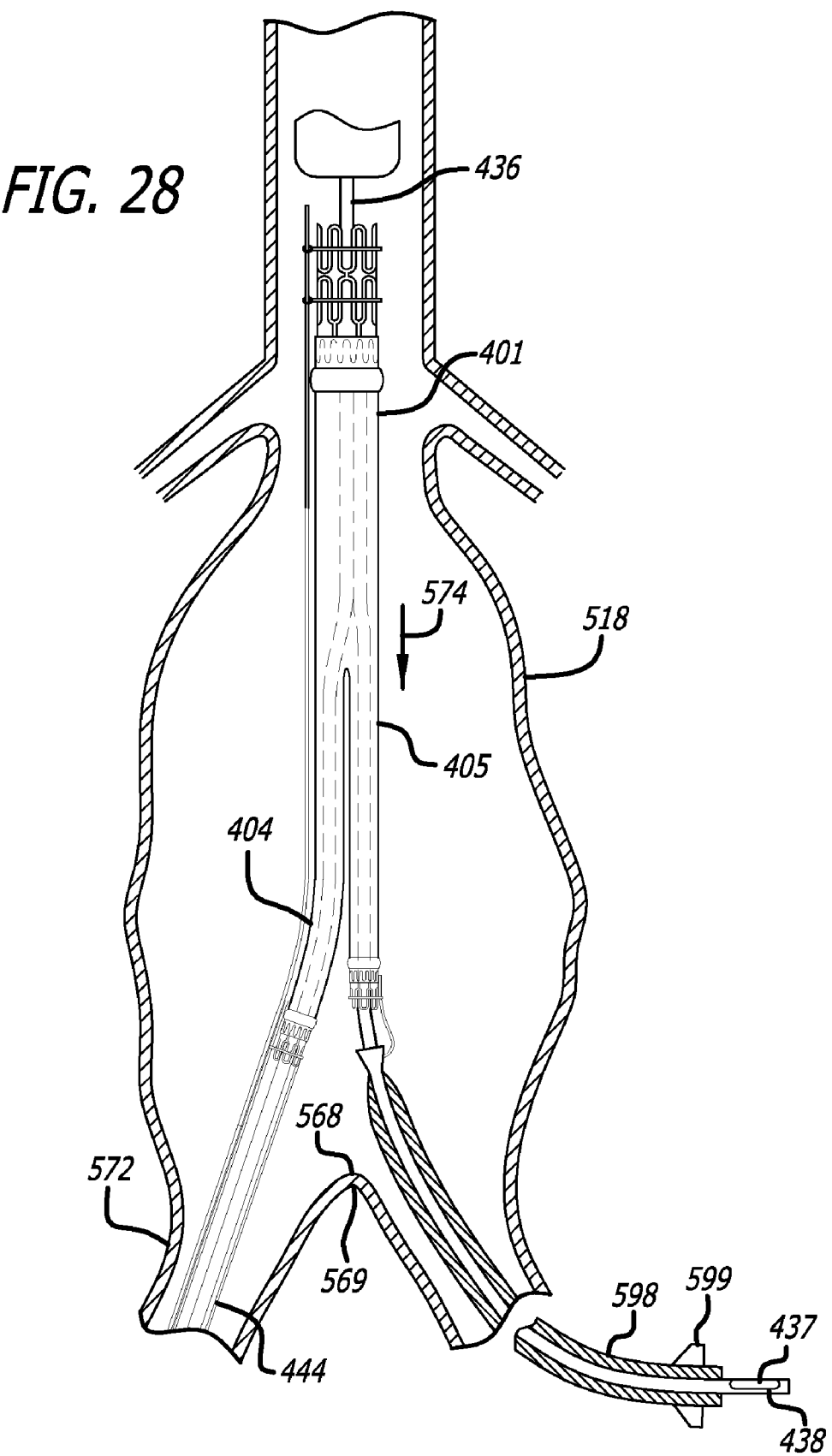
Figure 29:
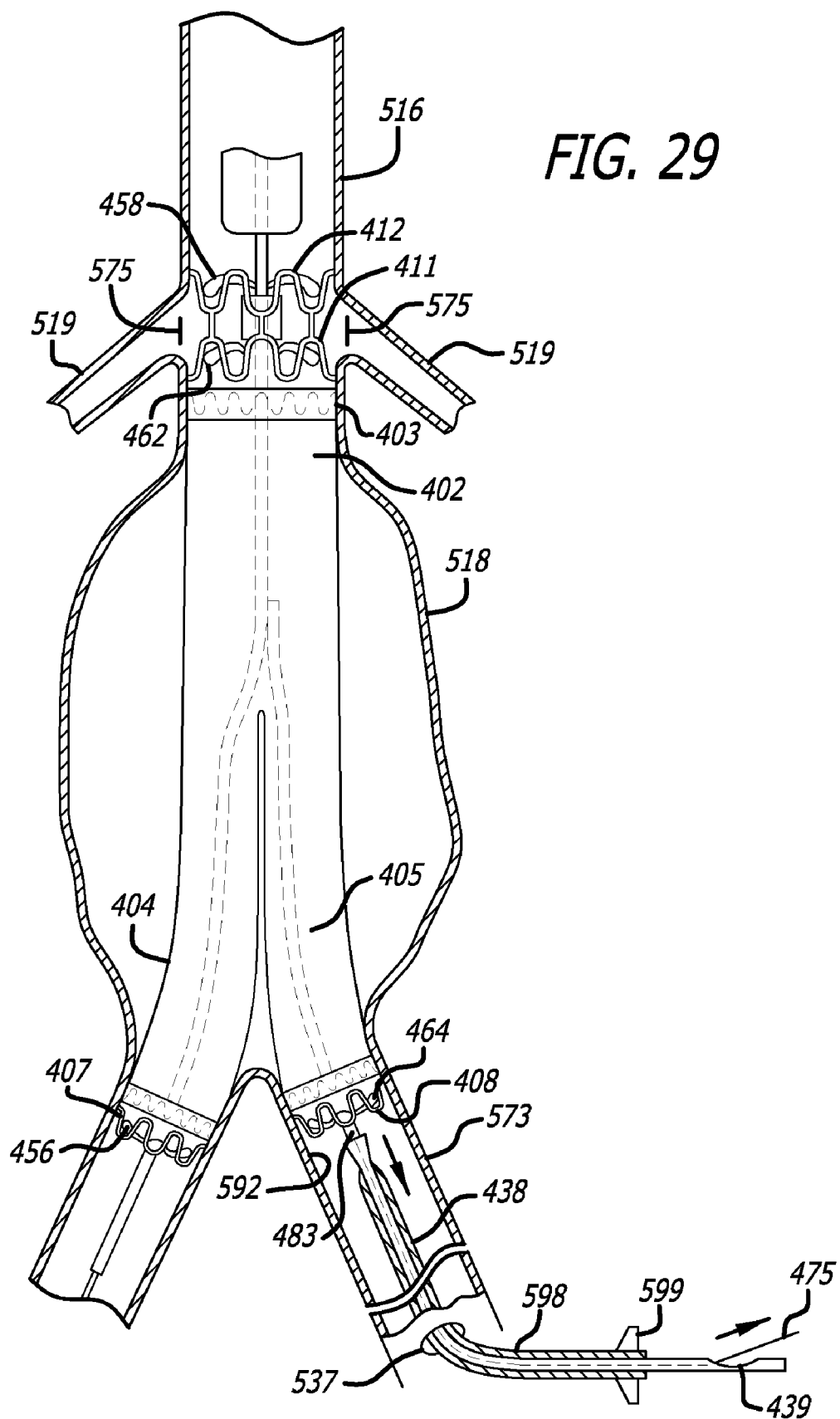
FIG. 29 is a side elevation view of the secondary delivery structure in accordance with one or more aspects of the invention.

Once the ipsilateral leg 404 of the graft 401 and contralateral leg 405 of the graft 401 are aligned with the right and left iliac arteries 572 and 573, respectively, the delivery system 400 may then be retracted proximally, as shown by the arrow 574 in FIG. 28, so as to reposition the distal section 426 of the elongate shaft 423 and the bifurcated graft 401 into the desired position for deployment as shown in FIG. 29.

When deploying the graft 401 in the abdominal aorta 516 it is generally desirable to ensure that the distal end 403 of the graft main body portion 402 is installed proximal to, or below, the renal arteries 519 in order to prevent their significant occlusion. However, the distal self-expanding members 411 and 422 of the graft 401 may, depending upon the anatomy of the patient and the location of the aneurysm 518, partially or completely span the ostia 575 of one or both renal arteries 519. It can be desirable, however, to ensure that ostia 575 of the renal arteries 519 are not blocked by the distal end 403 of the graft main body portion 402. As discussed previously, a variety of imaging markers may be used on either or both the delivery system 400 and the graft 401 itself to help guide the operator during the graft positioning process.

After proper positioning, the first and second distal self-expanding members 411 and 422 may then be deployed. The operator first unscrews or otherwise detaches a threaded portion of the distal primary release wire handle 495 and the distal primary release wire handle 495 is proximally retracted, which in turn retracts the distal primary release wire 442 in a proximal direction. As the distal end 582 of the distal primary release wire 442 passes through the end loops 472 and 473 of the first distal primary belt 458 and second distal primary belt 462, the end loops 472 and 473 are released, freeing the first distal self-expanding member 422 and second distal self-expanding member 411 to self-expand in an outward radial direction so to contact an inner surface 583 of the patient's aorta 516. The first and second distal primary belts 458 and 462 remain secured to the primary belt support member 452 and will eventually be retracted from the patient with the delivery system 400 after deployment is complete.

As the first and second distal self-expanding members 411 and 422 expand and contact the aorta 516, a distal end 403 of the graft main body portion 402 opens with the self-expanding members 411 and 422 and promotes opening of the graft polymer material portion from the flow of blood into the distal end 403 of the graft main body portion 402 with a "windsock" effect. As a result, once the first and second distal self-expanding members 411 and 422 are expanded to contact the aorta inner surface, the graft main body portion 402 and legs 404 and 405 balloon out or expand while the proximal ends 416 and 417 of the legs 404 and 405 of the graft 401 remain constricted due to the constrained configuration of the proximal self-expanding members 407 and 408 of the ipsilateral and contralateral legs 404 and 405. At this point, there typically will be partial or restricted blood flow through and around the graft 401.

Bifurcated graft 401 may then be optionally be inflated with an inflation material via inflation tube 444 and inflation port 421 until the inflatable channels 418 and inflatable cuffs 413, 414 and 415 have been filled to a sufficient level to meet sealing and other structural requirements necessary for the bifurcated graft main body portion 402 and the ipsilateral and contralateral legs 404 and 405 to meet clinical performance criteria. Inflating the graft 401 prior to deploying the proximal and distal self-expanding members 407 and 408, respectively, may be useful in anatomies where the vasculature is tortuous or angled.

Next, the proximal self-expanding member 407 of the ipsilateral leg 404 is deployed. Deployment of the first and second distal self-expanding member 411 and 422 has exposed the proximal primary release wire handle 496, making it accessible to the operator. The proximal primary release wire handle 496 is retracted proximally so as to deploy the proximal primary belt 456 and proximal self-expanding member 407 of the ipsilateral leg 404.

Figure 30:
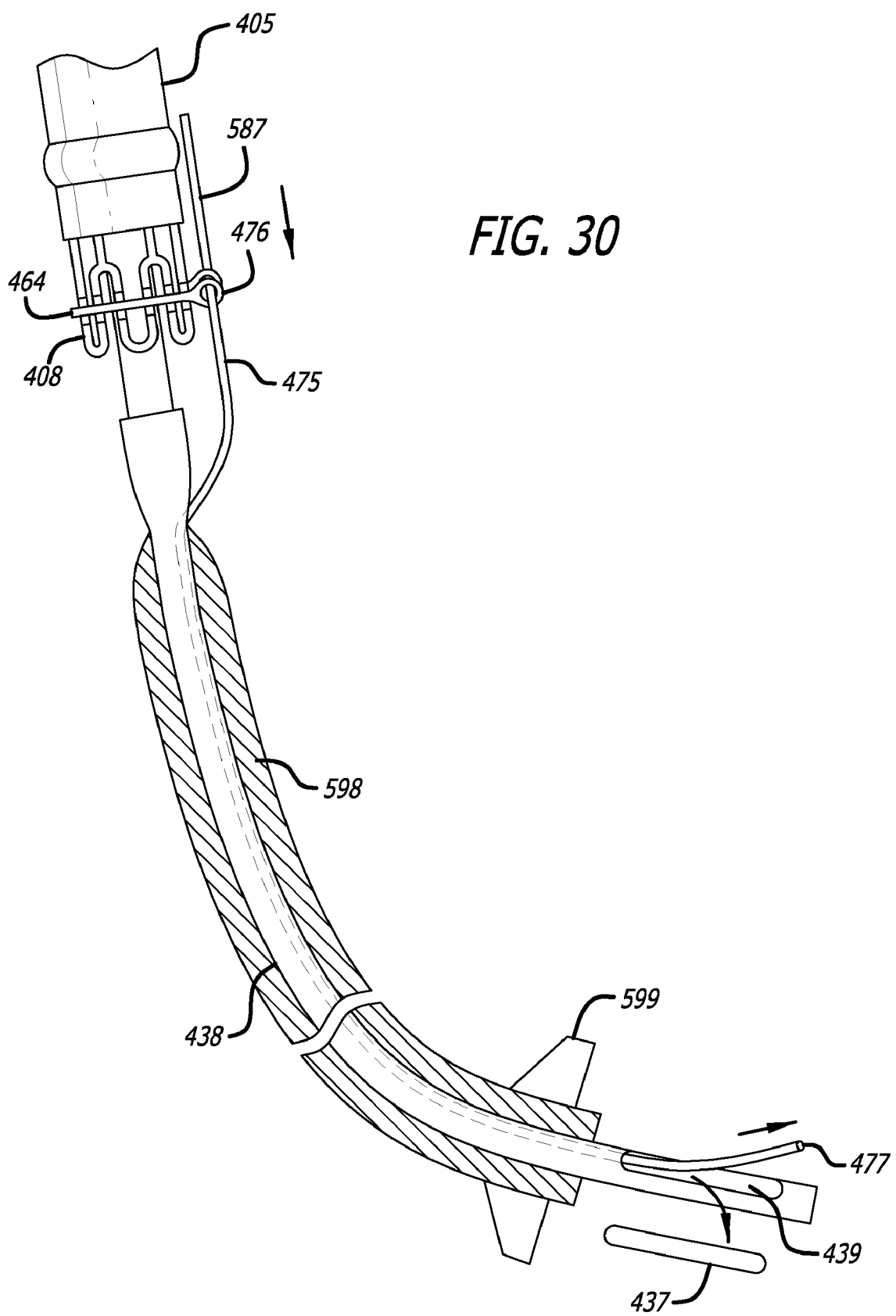
FIGS. 30-32 continue to illustrate a deployment sequence of the bifurcated endovascular stent graft delivery system of FIG. 2.
Figures 31, 32:
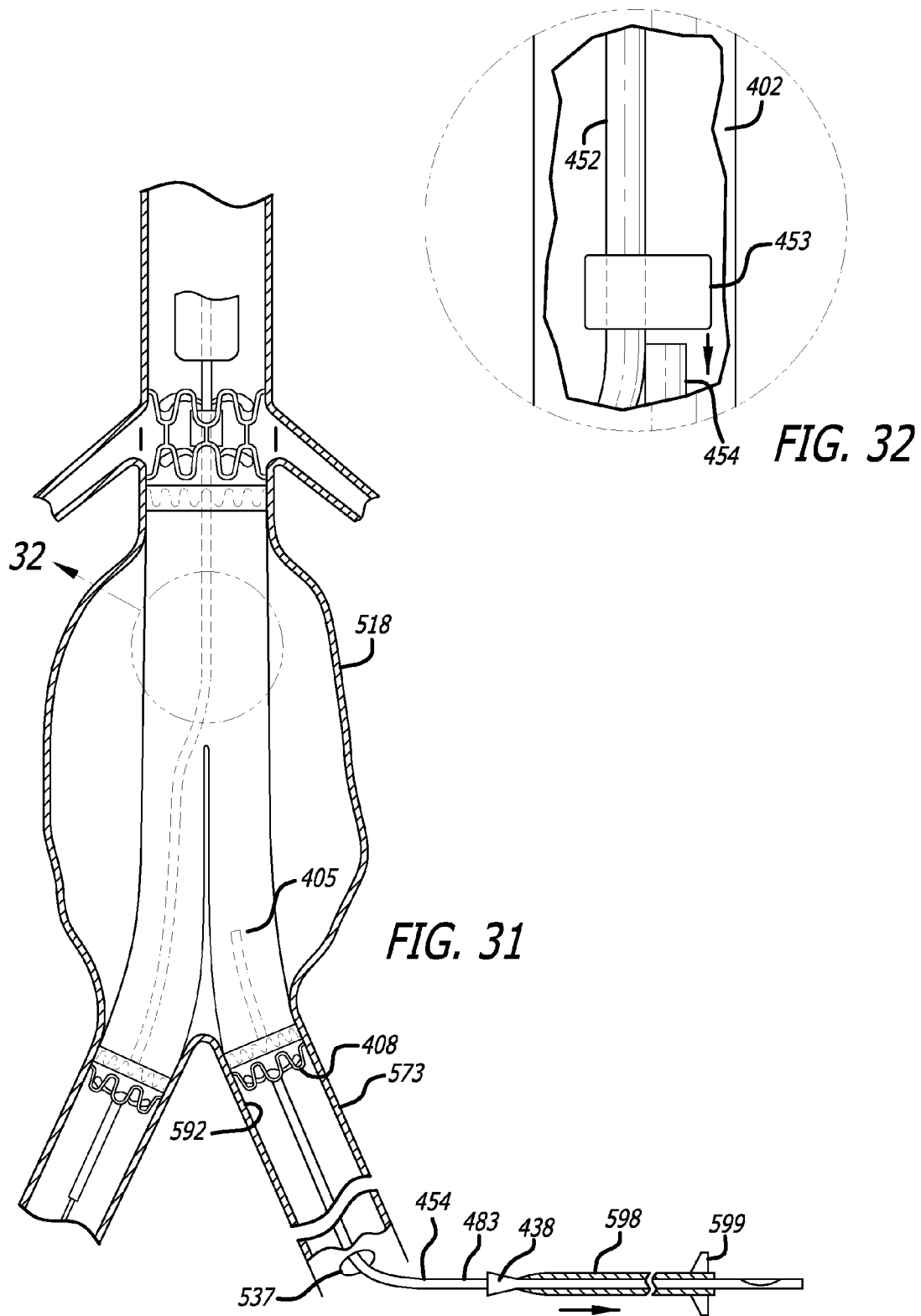

FIGS. 29 and 30 depict an enlarged view of the proximal end 483 of the secondary belt support member 454. The proximal self-expanding member 408 of the contralateral leg 405 is secured to the proximal end 417 of the contralateral leg 405. The proximal self-expanding member 408 is constrained in a radial direction by the secondary belt 464, which has end loops 476 releasably constrained by the distal end 587 of the secondary release wire 475. To access the proximal end 477 of the secondary release wire 475, the covering 437 over access opening 439 is peeled away. The proximal end of the secondary release wire 475 is accessed through the access opening 439 and the secondary release wire is pulled in the proximal direction to release the distal end 587 of the secondary release wire 475 from the end loops 468 of the secondary belt 464 so as to release the radial constraint on the proximal self-expanding member 408 imposed by the secondary belt 464. Upon release of the radial constraint, the proximal self-expanding member 408 expands so as to contact an inside surface 592 of the left iliac artery 573 as shown in FIG. 31. Once the proximal self-expanding member 408 of the contralateral leg 405 is expanded, the operator may then apply tension to the obturator 598 in the proximal direction to withdraw the obturator 598 which, through its connection, withdraws the release strand tube 438, which in turn, withdraws the secondary belt support member 454. As shown in FIG. 32, the secondary belt support member 454 slides from the housing 453 and is easily removed from the patient's vasculature through the left femoral artery access hole 537.

What is claimed is:

1. A delivery system for a bifurcated intracorporeal device comprising:
   a shaft having a distal section supporting:
   a primary support member positioned to be disposed within at least a primary portion of the bifurcated intracorporeal device; and
   a secondary support member adjacent the primary support member and positioned to be disposed within a secondary portion of the bifurcated intracorporeal device;
   at least one belt configured to be circumferentially disposed about a portion of the secondary support member so to at least partially constrain the secondary portion of the bifurcated intracorporeal device;
   a tube including a distal end which is directly connected to the secondary support member such that movement of the tube is translated to a corresponding force on the secondary support member; and
   a release member configured to engage and releasably secure the belt in a constraining configuration, the release member extending through at least a portion of the tube such that the release member is accessible adjacent a proximal end of the tube.

2. The delivery system of claim 1 wherein the bifurcated intracorporeal device is a bifurcated endovascular graft.

3. The delivery system of claim 1 wherein the release member comprises a release wire moveably disposed within opposed looped ends of the belt.

4. The delivery system of claim 1 further comprising a secondary support member housing secured to the primary support member wherein the secondary support member is configured to move axially within the housing and the housing and secondary support member are configured to prevent relative rotational movement therebetween.

5. The delivery system of claim 1 wherein the distal end of the tube is adhesively bonded to the secondary support member.

6. The delivery system of claim 1 wherein the distal end of the tube is welded to the secondary support member.

7. The delivery system of claim 1 wherein the distal end of the tube is formed integrally with the secondary support member.

8. The delivery system of claim 1 wherein a portion of the distal end of the tube is removed to define an enlarged opening into a tube lumen.

9. The delivery system of claim 1 wherein an access opening in communication with a tube lumen is formed adjacent the proximal end of the tube to facilitate access to the release wire.

10. The delivery system of claim 9 wherein the access opening is formed by cutting away a portion of the proximal end of the tube.

11. The delivery system of claim 9 wherein the access opening is formed by providing a skive portion of the proximal end of the tube which is broken open to provide access.

12. The delivery system of claim 9 further comprising a removable cover positioned over the access opening.

13. The delivery system of claim 9 further comprising a heat shrink wrap over at least a portion of the access opening.

14. The delivery system of claim 9 wherein the release member is bonded within the tube lumen proximal from the access opening.

15. The delivery system of claim 1 wherein the release member is bonded within a tube lumen adjacent the proximal end and the proximal end of the tube is releasably connected to an intermediate portion of the tube such that the release member is actuated by disconnecting the proximal end of the tube from the intermediate portion and moving the proximal end of the tube proximally relative to the intermediate portion.

16. The delivery system of claim 15 wherein the intermediate portion is formed integrally with the distal end of the tube.

* * * * *